US008812130B2

(12) United States Patent
Stahmann et al.

(10) Patent No.: US 8,812,130 B2
(45) Date of Patent: Aug. 19, 2014

(54) CONTROL OF NEURAL MODULATION THERAPY USING CERVICAL IMPEDANCE

(71) Applicant: Cardiac Pacemakers, Inc., St. Paul, MN (US)

(72) Inventors: Jeffrey E. Stahmann, Ramsey, MN (US); Stephen Ruble, Lino Lakes, MN (US); Jason J. Hamann, Blaine, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/761,372

(22) Filed: Feb. 7, 2013

(65) Prior Publication Data

US 2013/0204328 A1    Aug. 8, 2013

Related U.S. Application Data

(60) Provisional application No. 61/595,745, filed on Feb. 7, 2012.

(51) Int. Cl.
*A61N 1/05*    (2006.01)

(52) U.S. Cl.
USPC .......................................................... 607/62

(58) Field of Classification Search
USPC .......................................................... 607/62
See application file for complete search history.

(56) References Cited

U.S. PATENT DOCUMENTS

| | | | |
|---|---|---|---|
| 7,387,610 B2 | 6/2008 | Stahmann et al. | |
| 7,580,746 B2 | 8/2009 | Gilkerson et al. | |
| 7,647,114 B2 | 1/2010 | Libbus | |
| 7,664,548 B2 | 2/2010 | Amurthur et al. | |
| 7,848,812 B2 | 12/2010 | Crowley et al. | |
| 7,877,140 B2 | 1/2011 | Stahmann et al. | |
| 7,957,802 B2 | 6/2011 | Patangay et al. | |
| 7,974,693 B2 | 7/2011 | Ben-David et al. | |

(Continued)

FOREIGN PATENT DOCUMENTS

WO    WO-2013119732 A1    8/2013

OTHER PUBLICATIONS

Moderhak, M., et al., "Pulse pressure velocity measurement—A wearable sensor", Proceedings of the Federated Conference on Computer Science and Information Systems, (2011), 411-146.

(Continued)

*Primary Examiner* — George Manuel
(74) *Attorney, Agent, or Firm* — Schwegman Lundberg & Woessner, P.A.

(57) ABSTRACT

An implantable apparatus can comprise an electrical test energy delivery circuit configured to provide an electrical test signal to a cervical location in a patient body. A detector circuit can use the electrical test signal to detect cervical impedance and generate a cervical impedance signal representing fluctuations in the detected cervical impedance. The implantable apparatus can comprise a therapy delivery circuit, such as configured to provide electrical neural modulation therapy using a neural modulation timing parameter, and a processor circuit that can be coupled to the electrical test energy delivery circuit, the detector circuit, and the therapy delivery circuit. The processor circuit can be configured to determine a pulsatile signal or pulse pressure signal, such as using the cervical impedance signal, identify a characteristic of the pulsatile signal or pulse pressure signal, and control a neural modulation therapy using the timing parameter and the identified pulse pressure signal characteristic.

20 Claims, 12 Drawing Sheets

(56) References Cited

U.S. PATENT DOCUMENTS

| | | | |
|---|---|---|---|
| 8,005,543 | B2 | 8/2011 | Libbus et al. |
| 8,046,069 | B2 | 10/2011 | Kramer et al. |
| 8,116,873 | B2 | 2/2012 | Anderson et al. |
| 8,150,512 | B2 * | 4/2012 | Bornzin et al. .................. 607/8 |
| 8,214,050 | B2 | 7/2012 | Kieval |
| 8,326,430 | B2 | 12/2012 | Gerogakopoulos et al. |
| 8,620,422 | B2 | 12/2013 | Kieval et al. |
| 2006/0074453 | A1 | 4/2006 | Kieval et al. |
| 2006/0265038 | A1 | 11/2006 | Hagen et al. |
| 2008/0140167 | A1 | 6/2008 | Hagen et al. |
| 2008/0167693 | A1 | 7/2008 | Kieval et al. |
| 2008/0177365 | A1 | 7/2008 | Bolea et al. |
| 2009/0018596 | A1 | 1/2009 | Kieval |
| 2009/0198302 | A1 | 8/2009 | Anderson et al. |
| 2009/0228078 | A1 | 9/2009 | Zhang et al. |
| 2010/0228310 | A1 | 9/2010 | Shuros et al. |
| 2011/0118802 | A1 | 5/2011 | Usui |
| 2011/0224750 | A1 | 9/2011 | Scheiner |
| 2011/0257708 | A1 | 10/2011 | Kramer et al. |

OTHER PUBLICATIONS

Stahmann, Jeffrey E, et al., "Method and Apparatus for Determination of Physiological Parameters Using Cervical Impedance", U.S. Appl. No. 61/522,047, filed Oct. 28, 2011, 57 pages.

International Application Serial No. PCT/US2013/025025, International Search Report mailed Apr. 16, 2013, 4 pgs.

International Application Serial No. PCT/US2013/025025, Written Opinion mailed Apr. 16, 2013, 9 pgs.

* cited by examiner

CONTROL OF NEURAL MODULATION THERAPY USING CERVICAL IMPEDANCE

CLAIM OF PRIORITY

This application claims the benefit of priority under 35 U.S.C. §119(e) of Stahmann et al., U.S. Provisional Patent Application Ser. No. 61/595,745, entitled "CONTROL OF NEURAL MODULATION THERAPY USING CERVICAL IMPEDANCE", filed on Feb. 7, 2012, which is herein incorporated by reference in its entirety.

BACKGROUND

Neural stimulation, such as vagus nerve stimulation, has been proposed as a therapy for a number of conditions. Examples of neural stimulation therapies include neural stimulation therapies for respiratory problems such as sleep disordered breathing, blood pressure control such as to treat hypertension, cardiac rhythm management, myocardial infarction and ischemia, heart failure (HF), epilepsy, depression, pain, migraines, eating disorders and obesity, and movement disorders.

OVERVIEW

Some embodiments, by way of example and not limitation, provide an implantable apparatus. For example, the implantable apparatus can include an electrical test energy delivery circuit and a detector circuit. The electrical test energy delivery circuit can be configured to provide a non-neurostimulating electrical test signal to a cervical location in a patient body (e.g., at or near a patient neck region), such as using an implanted electrode. The detector circuit can be configured to use the electrical test signal to detect cervical impedance or to generate a cervical impedance signal representing fluctuations in the detected cervical impedance over time. The fluctuations in the detected cervical impedance can correspond to dimensional changes of a blood vessel, such as a carotid artery or jugular vein. Such fluctuating, dimensional changes can be used to determine pulsatile information, which is information related to cardiac activity and/or information related to the pulsing blood through the patient's cardiovascular system. For example, the cervical impedance can be used to determine one or more physiological parameters, such as heart rate, phases of a blood pressure cycle, phases of a cardiac cycle, a pulse transit time, relative pulse pressure, or arterial compliance, among others. In some examples, these and other parameters can be used to monitor a patient health status or to modulate a patient therapy, among other uses.

In an example, the implantable apparatus can comprise a therapy delivery circuit configured to provide electrical neural modulation therapy to a patient using an implanted electrode and a neural modulation timing parameter. In an example, the implantable apparatus can comprise a processor circuit, such as can be coupled to an electrical test energy delivery circuit, a detector circuit, and a therapy delivery circuit. The processor circuit can be configured to determine pulsatile information from a cervical impedance signal, identify at least one feature of the pulsatile information, and control delivery of a neural modulation therapy using the neural modulation timing parameter and the at least one identified feature of the pulsatile information from the cervical impedance signal.

Various embodiments can be used to identify an appropriate, or beneficial, delivery time for neural modulation therapy, such as can be used to mimic or enhance a natural patient physiological response. Various embodiments use cervical impedance information, such as a change in cervical impedance, to identify a pulsatile signal, or a blood pressure change in a blood vessel, and initiate or adjust a neural modulation therapy in response to the identified signal or pressure change. Various embodiments use one or more features of a cervical impedance or pulsatile signal (e.g., a local peak of a signal waveform) to adjust a neural modulation therapy parameter, such as a neural modulation therapy timing parameter.

This overview is intended to provide an overview of some of the teachings of the present application and is not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and are not intended to be exhaustive or exclusive embodiments of the present subject matter.

DETAILED DESCRIPTION

Figure 1:
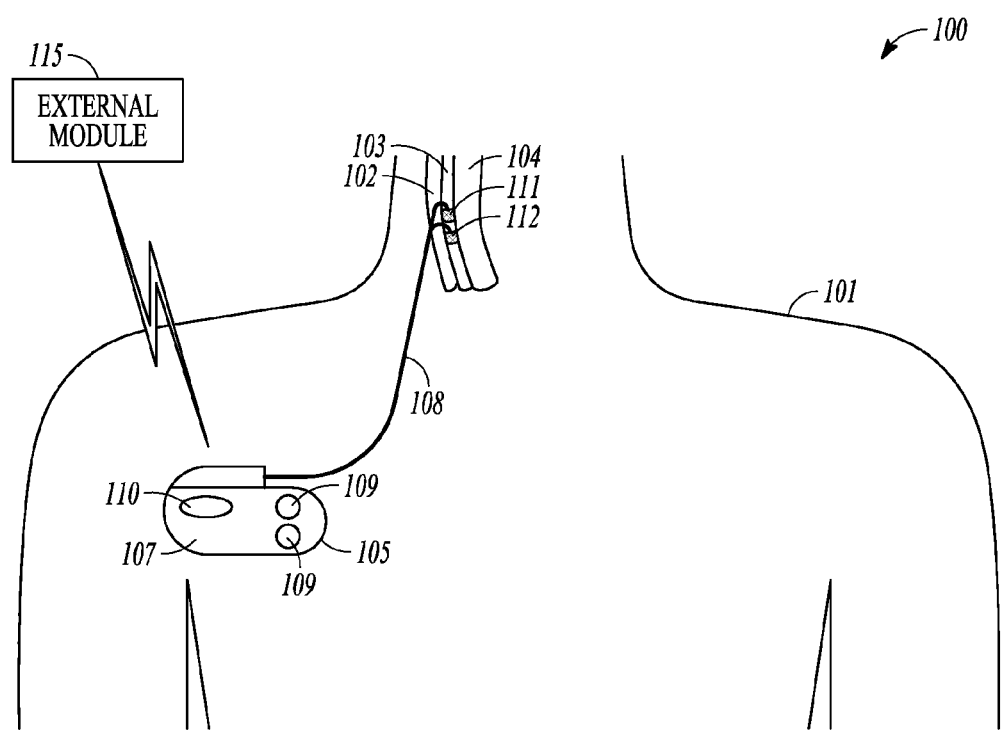
FIG. 1 illustrates generally an example that can include an ambulatory medical device and an external module.

The following detailed description of the present subject matter refers to the accompanying drawings which show, by way of illustration, specific aspects and examples in which the present subject matter may be practiced. The examples are described in sufficient detail to enable those skilled in the art to practice the present subject matter. Other examples may be utilized, and structural, logical, and electrical changes may be made without departing from the scope of the present subject matter. References to "an", "one", or "various" examples in this disclosure are not necessarily to the same example, and such references contemplate more than one example. The following detailed description is, therefore, not to be taken in a limiting sense, and the scope is defined only by the appended claims, along with the full scope of legal equivalents to which such claims are entitled.

The autonomic nervous system (ANS) regulates "involuntary" organs (in contrast to the somatic nervous system, responsible for volitional body system control, e.g., the contraction of skeletal muscles. Examples of involuntary organs can include respiratory and digestive organs, and can also include blood vessels and the heart. Often, the ANS functions in an involuntary, reflexive manner to regulate glands, to regulate muscles in the skin, eye, stomach, intestines or bladder, or to regulate cardiac muscle and the muscle cells around blood vessels, for example.

The ANS includes the sympathetic nervous system and the parasympathetic nervous system. The sympathetic nervous system is affiliated with stress and a "fight or flight response." Among other effects, the "fight or flight response" can increase blood pressure and heart rate, such as to increase skeletal muscle blood flow, and can decrease digestion to provide energy for "fighting or fleeing." The parasympathetic nervous system is affiliated with relaxation and a "rest and digest response" which, among other effects, decreases blood pressure and heart rate, and increases digestion to conserve energy. In a healthy person, the ANS maintains normal internal bodily functions and works in concert with the somatic nervous system.

Electrical neural stimulation therapy can be provided to stimulate the sympathetic or parasympathetic nervous systems, such as to treat a variety disorders. Neural stimulation therapy can be provided in coordination with a patient's physiological cycle to mimic or enhance a patient's natural response to physiological changes. In an example, a physiological cycle can be identified using fluctuations in measured cervical impedance over time. In some examples, patient pulsatile information can be determined using a measured impedance, such as pulsatile information about a cervical blood vessel (e.g., a carotid artery). Characteristics or features of the cervical impedance or pulsatile information can be used to identify portions of a patient's physiological cycle and to time delivery of neural stimulation therapies in coordination with the physiological cycle. For example, a pulsatile signal waveform can be generated using the pulsatile information, and neural stimulation therapy can be provided in coordination with an identified peak of the pulsatile signal waveform.

Stimulating the sympathetic and parasympathetic nervous systems can have physiological effects manifested many ways. Heart rate or cardiac contractility can increase in response to sympathetic nervous system stimulation, or can decrease in response to inhibition of the sympathetic nervous system (or in response to stimulation of the parasympathetic nervous system). For example, depending upon the site of stimulation, stimulating the sympathetic nervous system can dilate a pupil, reduce saliva and mucus production, relax the bronchial muscle, reduce successive waves of involuntary contraction (peristalsis) of the stomach and the motility of the stomach, increase conversion of glycogen to glucose by the liver, decrease urine secretion by the kidneys, or constrict the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intestine, increases urine secretion, and contracts the wall and relaxes the sphincter of the bladder. The functions associated with the sympathetic and parasympathetic nervous systems are many and can be complexly integrated with each other.

Neural stimulation may be used to treat a variety of cardiovascular disorders, including heart failure, post-MI remodeling, or hypertension. These conditions are briefly described below.

Heart failure refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have impaired autonomic balance, which is associated with LV dysfunction and increased mortality.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Implantable or ambulatory medical devices or systems can interact with nerve tissue in a subject body. FIG. 1 illustrates generally an example of a system 100, including an implantable medical device (IMD) 105 that can be placed subcutaneously or submuscularly in a subject body 101, and can be configured to interact with nerve tissue in the subject body 101. For example, the IMD 105 can be configured to use patient physiological information, such as patient pulsatile information or other patient activity information, to time delivery of an electrical neural modulation therapy using the sensed patient information.

The IMD 105 can include a conductive housing 107 or a processor circuit 110, such as can be operably connected to one or more stimulating or sensing circuits. The IMD 105 may be configured to operate autonomously with all circuitry residing within the IMD 105, and/or may be configured to operate with one or more other devices (e.g., IMD(s) and/or external device(s) such as a programmer or an analyzer circuit). For example, the IMD 105 may be configured to deliver neural stimulation therapy and to communicate with a cardiac rhythm management (CRM) device, such as a pacemaker or defibrillator, which is configured to sense physiological parameter(s) or response(s) and provide cardiac rhythm management therapy. The IMD 105 can use these sensed physiological parameter(s) or response(s) to control the neural stimulation or to provide diagnostic information for the patient condition and the efficacy of the neural stimulation. In an example, a CRM device can use information from the IMD 105, such as information about a neural modulation therapy (e.g., information about a timing of a neural modulation therapy) to control the cardiac rhythm management functions of the CRM device. In some examples, the IMD 105 can be equipped to provide both neural stimulation and CRM therapies. Combined cardiac and neuromodulation devices are further described in Amurthur et al., U.S. Pat. No. 7,664,548, entitled DISTRIBUTED NEUROMODULATION SYSTEM FOR TREATMENT OF CARDIOVASCULAR DISEASE, Libbus et al., U.S. Pat. No. 7,647,114, entitled BAROREFLEX MODULATION BASED ON MONITORED CARDIOVASCULAR PARAMETER, and in Libbus et al., U.S. Pat. No. 8,005,543, entitled HEART FAILURE MANAGEMENT SYSTEM, which are incorporated herein by reference in their entirety.

In an example, the IMD 105 can include a communication circuit and antenna, or telemetry coil, such as can be used to communicate wirelessly with an external module 115 or other device. The system 100 can include one or more leadless ECG electrodes 109 or other electrodes, such as can be disposed on the housing of the IMD 105. These electrodes can be used to detect heart rate or cardiac arrhythmias, among other characteristics of a cardiac cycle.

The external module 115 can include a remote medical device programmer or one or more other remote external modules (e.g., outside of wireless communication range of the IMD 105 antenna, but coupled to the IMD 105 using an external device, such as a repeater or network access point). The external module 115 can include a processor circuit configured to process information that can be sent to or received from the IMD 105. The information can include medical device programming information, subject data, device data, instructions, alerts, or other information. In an example, the external module 115 can be configured to display information (e.g., information received from the IMD 105) to a user. Further, the local programmer or the remote programmer can be configured to communicate the sent or received information to a user or physician, such as by sending an alert (e.g., via e-mail) of the status of the subject 101 or the system 100.

In an example, such as shown in FIG. 1, the IMD 105 can be coupled to an implantable lead system 108. The implantable lead system 108 can include at least one neural stimulation lead that can be subcutaneously implanted to position electrode(s) to stimulate a neural target in a cervical region (e.g., a region at or near the neck) in the subject body 101. Examples of cervical neural targets include a vagus nerve, a carotid sinus nerve, a hypoglossal nerve, a glossopharyngeal nerve, a phrenic nerve, baroreceptors and the nerves that innervate and are proximate to the baroreceptors, and chemoreceptors and the nerves that innervate and are proximate to the chemoreceptors. The neural target may be on the left side (e.g. left vagus nerve), or the right side (e.g. right vagus nerve). Additionally, bilateral neural targets may be stimulated. Other neural stimulation lead(s) can include electrodes configured to stimulate neural targets outside of a cervical region. For example, an electrode can be configured to stimulate a vagus nerve near the stomach.

Implanted electrode(s) disposed proximal to or in contact with a neural target can be used to provide neural electrostimulation. A first electrode 111, such as a first nerve cuff electrode, can be disposed at the end of the neural stimulation lead. In an example, the first electrode 111 can include a nerve cuff electrode that can be sized, shaped, or otherwise configured to be disposed around a vagus nerve 103. One or more additional nerve cuff electrodes, such as a second electrode 112, can be similarly provided. In an example, neural stimulation may be provided using the first and second electrodes 111 and 112 in a bipolar configuration.

Some other vagus nerve stimulation examples can include one or more electrodes that can be sized, shaped, or otherwise configured to be fed into a vessel near the vagus nerve 103, such as for using electrodes positioned within the vessel to intravascularly stimulate the neural target. For example, a neural target can be stimulated using at least one electrode positioned internally within a jugular vein 102 or a carotid artery 104. The neural stimulation may be bipolar stimulation or unipolar stimulation, such as where the conductive housing 107 of the IMD 105 functions as an electrode.

As discussed above, an implantable electrode can be configured to deliver an electrical neural modulation therapy to one or more of a hypoglossal nerve, a glossopharyngeal nerve, a carotid sinus nerve, or vagus nerve in the cervical region. In an example, an electrical neural modulation therapy can additionally or alternatively be delivered to other sympathetic or parasympathetic neural targets, including peripheral neural targets or spinal neural targets. In an example, electrical neural modulation therapy can be delivered to one or more spinal nerves, such as including in the cervical, thoracic, lumbar, or sacral spinal cord regions. In an example, an electrical neural modulation therapy can additionally or alternatively be delivered to baroreceptor targets, such as to baroreceptor targets in a carotid sinus or pulmonary artery, among other locations. In some examples, an electrical neural modulation therapy can alternatively or additionally be delivered to chemoreceptor targets. One or more other neural targets, such as including cardiac nerves or cardiac fat pads can additionally or alternatively be stimulated. For example, electrodes configured to deliver a kidney therapy can be disposed at or near a renal nerve and a renal artery. In an example, some electrodes configured to deliver a bladder therapy can be disposed at or near a sacral nerve and a sacral artery.

Other examples can include delivering electrical neural stimulation from within the trachea, or within a blood vessel in close proximity to a nerve, such as within the internal jugular vein, the superior vena cava, or the azygous, brachiocephalic, or the subclavian veins. Electrical neural stimulation may be delivered using electrode(s) positioned within a lymphatic vessel. In some cases, a neural target can be stimulated using ultrasound or light energy. In an example, the system 100 can include one or more satellite electrodes that can be positioned to stimulate a neural target. The satellite electrodes can be coupled to the IMD 105 using a wireless link, such as to provide a stimulation or communication signal.

Figure 2:
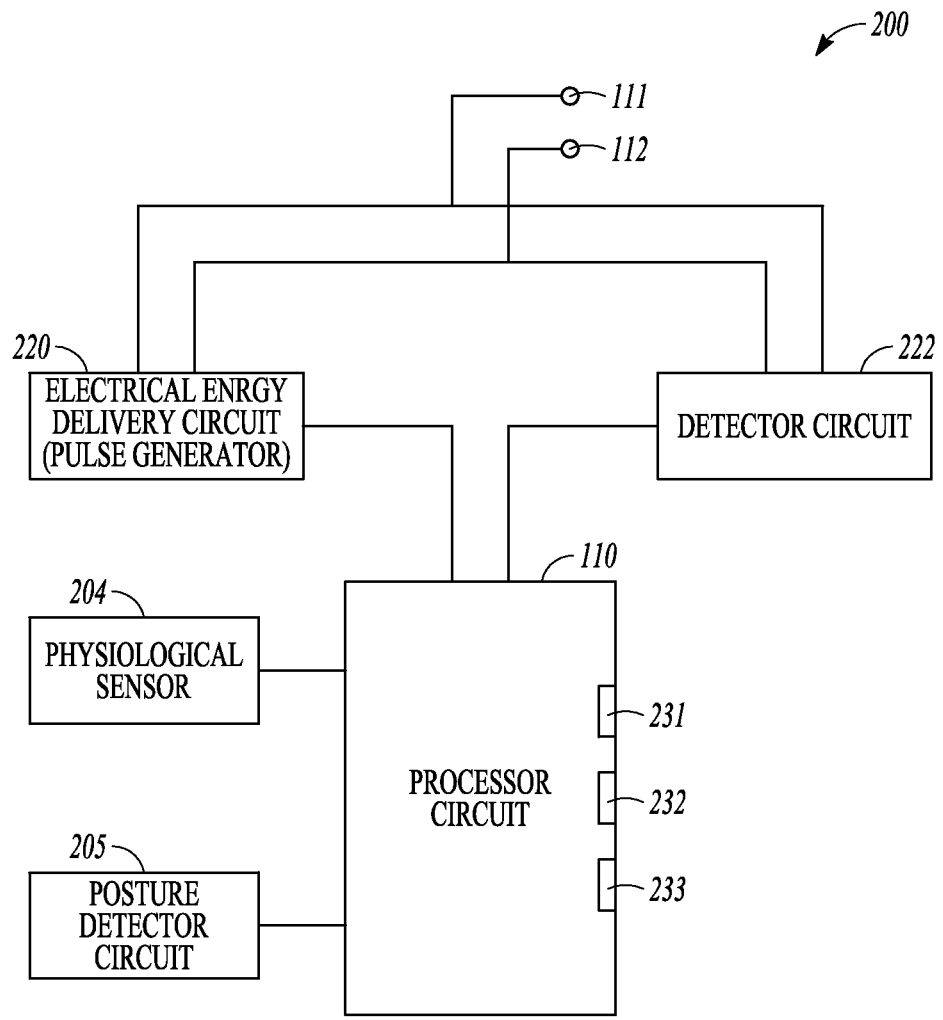
FIG. 2 illustrates generally an example that can include a processor circuit, an energy delivery circuit, or a detector circuit.

FIG. 2 illustrates generally an example of a system 200 that can comprise a portion of the system 100, such as including the IMD 105 and one or more electrode leads. The system 200 can be used to receive and interpret patient physiological information, such as including cervical impedance information, and time delivery of a neural stimulation or modulation therapy using the patient physiological information.

In the example of FIG. 2, the processor circuit 110 can include multiple data inputs or outputs 231, 232, or 233. Other data inputs or outputs of the processor circuit 110 can be coupled to one or more of a physiological sensor 204, a posture detector circuit 205, a detector circuit 222, or an electrical energy delivery circuit 220, or another circuit or device. In an example, the data input/output 231 can be configured to receive a signal representative of electrical activity of the heart of the subject 101. For example, the input/output 231 can be configured for use with a device capable of measuring an ECG or other patient electrical activity.

The physiological sensor 204 can include a posture sensor, a heart rate sensor, a respiration rate sensor, a respiratory phase sensor, a patient physical activity level sensor, an accelerometer, or a cardiac arrhythmia sensor, or another type of sensor. The sensor can be configured to provide, to the processor circuit 110, a signal indicative of a patient physiological parameter, or indicative of a change in a patient physiological parameter.

The electrical energy delivery circuit 220 can comprise a pulse generator that can be coupled to one or more electrodes (e.g., the first or second electrodes 111 or 112, or the conductive housing 107), such as including an implantable cuff electrode disposed around a neural target. The electrical energy delivery circuit 220 can be configured to generate a current pulse or provide a current pulse to the one or more electrodes, such as in response to a control signal provided by the processor circuit 110. For example, under control of the processor circuit 110, the electrical energy delivery circuit 220 can generate and provide a current pulse to the first electrode 111, such as in response to a trigger signal received from the physiological sensor 204. In an example, the processor circuit 110 can be configured use information about a patient physiological cycle, such as pulsatile information derived from a patient cervical impedance signal, to initiate or adjust a neural modulation therapy, such as an electrical neural modulation therapy that can be provided using the electrical energy delivery circuit 220.

In an example, the detector circuit 222 can be configured to receive electrical signals from one or more electrodes, such as the first or second electrodes 111 or 112, or the conductive housing 107. In an example, the detector circuit 222 can be configured to receive or measure at least one of a current, voltage, or impedance signal in or on the subject body 101. The measured current, voltage, or impedance signal received by the detector circuit 222 can be received by the processor circuit 110 for further processing. In an example, the received or measured information can be passed from the processor circuit 110 to a different, second processor circuit, such as using the data input/output 231. For example, the received or measured information can be transferred to the external module 115 for further analysis, processing, or for display to a patient or physician. In an example, the detector circuit 222 can be used to detect one or more physiological parameters or responses, such as including blood pressure, cardiac activity parameters such as heart rate, and respiration parameters such as tidal volume or minute ventilation.

In an example, the electrical energy delivery circuit 220 can be configured to use a constant current source to deliver a current signal between two or more electrodes, such as can be disposed in a cervical, thoracic, or other body region, proximal to a nerve. The detector circuit 222 can be configured to detect a responsive voltage signal using the same or different electrodes. Fluctuations in the responsive voltage signal can be analyzed (e.g., using plethysmography techniques), such as to determine pulsatile information indicative of a change in a blood vessel dimension.

Figure 3:
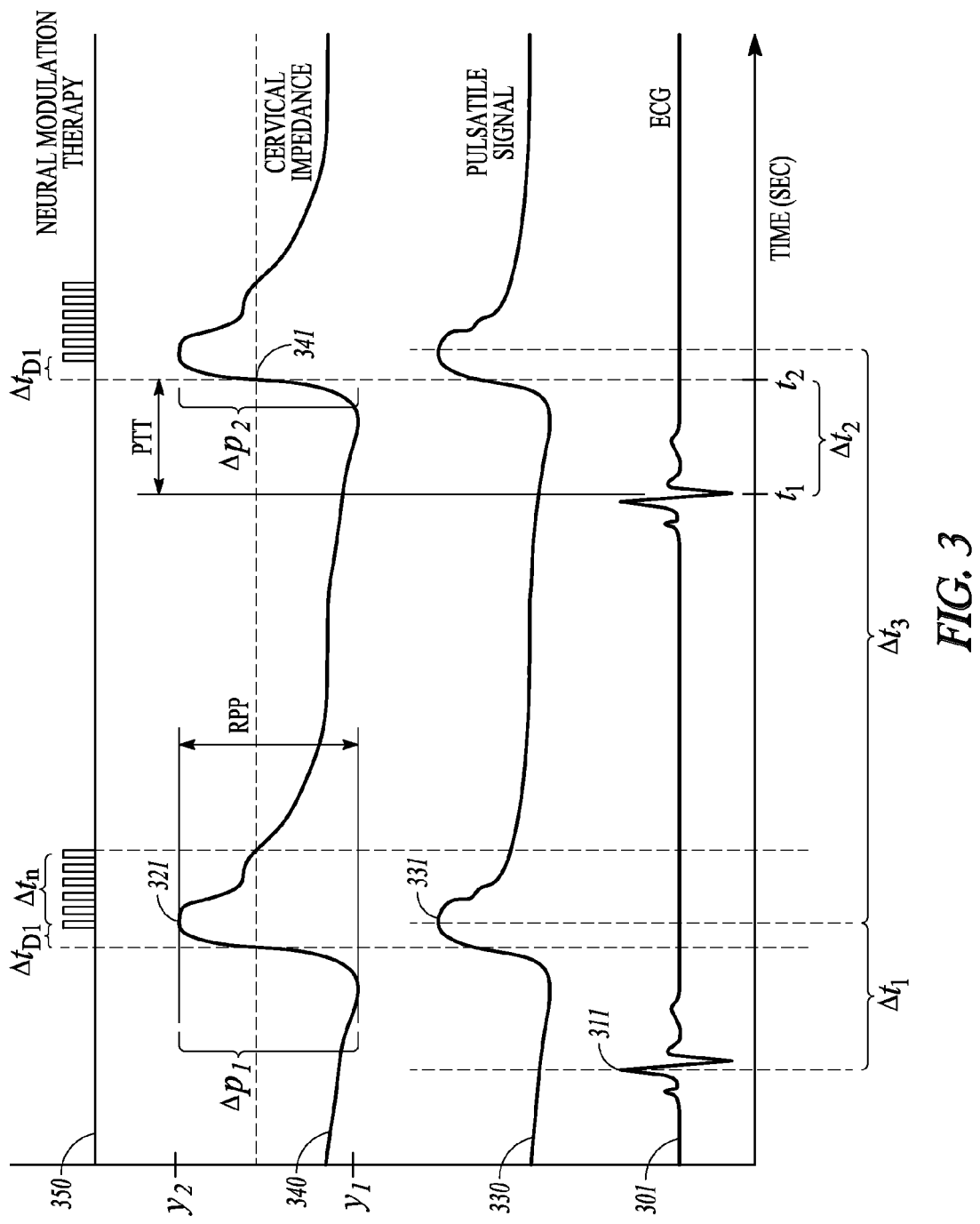
FIG. 3 illustrates generally an example of an ECG waveform with a corresponding cervical impedance waveform, a corresponding pulsatile signal waveform, and a neural modulation therapy scheme.

FIG. 3 illustrates generally several corresponding waveforms indicative of physiological patient activity, such as including an ECG waveform 301, a corresponding pulsatile signal waveform 330, or a corresponding cervical impedance waveform 340. In an example, a blood vessel impedance signal can be included. One or several of the corresponding waveforms can be measured using various systems or devices, such as using the system 200. The several waveforms can be illustrated using a common origin and time axis, as shown. FIG. 3 further illustrates an adjustable neural modulation therapy scheme 350, such as can correspond to one or more indications of physiological patient activity.

In an example, such as shown in FIG. 3, an ECG waveform 301 can be obtained, such as using at least two leadless ECG electrodes disposed on the housing of the IMD 105. In an example, the ECG waveform 301 can be obtained using a device other than the IMD 105, such as using an external monitoring device.

In an example, such as shown in FIG. 3, a cervical impedance waveform 340 can be obtained, such as using one or more electrodes disposed in a patient's cervical region. For example, the cervical impedance waveform 340 can be obtained using a bipolar electrode configuration, such as using the first and second electrodes 111 and 112 illustrated in the system 100, among other configurations. In an example, fluctuations in the cervical impedance waveform 340 can be correlated to cardiac activity. The fluctuations can be used to determine a patient heart rate or a patient heart rate signal. In an example, fluctuations in the cervical impedance waveform 340 can be correlated to fluctuations in a blood vessel dimension, such as can be used to obtain a blood vessel expansion signal or pulsatile signal.

The pulsatile signal waveform 330 can be measured using, among other techniques, sonomicrometry or impedance plethysmography. For example, the pulsatile signal waveform 330 can be derived using plethysmography analysis techniques and cervical impedance information, such as using the cervical impedance waveform 340. In an example, a physiological blood pressure sensor (e.g., the physiological sensor 204) can be disposed in or near the carotid artery 104, such as can be used to provide pulse pressure information to determine pulsatile information (e.g., including the pulsatile signal waveform 330). The pulsatile signal waveform 330 can indicate, among other things, a relative change in a diameter or portion of a diameter of a blood vessel, such as over one or more cardiac cycles.

Various physiological parameters can be used to determine or provide pulsatile information, such as can be used to form the pulsatile signal waveform 330. For example, pulsatile information can include information about one or more of a patient blood pressure, pulse pressure, relative pulse pressure, phase of a blood pressure cycle, or heart sounds. Other parameters or information can be derived using pulsatile information (e.g., using the pulsatile signal waveform 330), such as including heart rate, pulse transit time, or arterial compliance information.

In the example of FIG. 3, changes in blood vessel impedance, thoracic impedance, or cervical impedance can correspond with changes in a blood vessel dimension. For example, information obtained from a blood vessel impedance signal (not shown in FIG. 3) can be used to derive dimensional information about a blood vessel, such as including information about a presence or passage of a blood pressure pulse. In an example, a relative maximum blood vessel impedance, such as corresponding to a first cardiac cycle, can precede a corresponding relative maximum 331 of the pulsatile signal waveform 330, such as by a time $\Delta t$. Subsequent relative maximum and minimum impedances can similarly correspond to respective relative maxima and minima of the pulsatile signal waveform 330 such that the blood vessel impedance signal can be an effective surrogate indication of pulsatile fluctuations (e.g., pulse pressure fluctuations), or vice versa.

Information about a patient physiological status can be discerned using one or more of the waveforms illustrated in FIG. 3. In an example, relationships between or among waveform characteristics can provide information about a patient health status. For example, information about a pulsatile signal amplitude or about timing of adjacent peaks of the pulsatile signal waveform 330 can provide information about a patient health status. For example, a relative maximum of the ECG signal 301 (e.g., a peak of an R-wave) and a relative maximum of the pulsatile signal waveform 330 can be offset by a time of about $\Delta t_1$. In an example, $\Delta t_1$ can be used to provide information about a patient physiological status or to trigger a patient therapy, such as in response to a lengthening interval $\Delta t_1$. In an example, lengthening $\Delta t_1$ can indicate a worsening dissynchrony between cardiac electrical activity and a patient pulse pressure.

In an example, information about a patient physiological status or a patient physiological activity can be used to coordinate delivery of a neural modulation therapy. For example, one or more patient physiological events, patient physiological cycle characteristics, or other indications of patient physiological activity can be used to coordinate delivery of a neural modulation therapy. Patient physiological activity can be identified using one or more of the pulsatile signal waveform 330, the cervical impedance waveform 340, the ECG waveform 301, or some other indication of a patient physiological activity. In an example, a waveform characteristic can be used to identify a patient physiological event or to identify a portion of a patient physiological cycle, such as can trigger a neural modulation therapy. In an example, one or more neural modulation therapy parameters can be adjusted in response to an identified patient physiological activity. A neural modulation therapy parameter can be used to define or determine one or more neural modulation therapy characteristics, such as a neural modulation therapy pulse characteristic (e.g., amplitude, duration, etc.).

In an example, the pulsatile signal waveform 330 or the cervical impedance waveform 340 can be used to determine several physiological events or cycle characteristics, such as including blood pressure, pulse pressure, pulse transit time (PTT), or relative pulse pressure (RPP), among others. Such indications of physiological activity can be used to provide information about a patient physiological status, such as information about heart rate, arterial compliance or stiffness, cardiac contractility, autonomic status, pulmonary vein distension, respiratory effort or disturbance (e.g., including apnea), blood pressure cycle phase, or a patient fluid status, among other things. Such information can be used to monitor a health patient status, to provide information for patient diagnostics, or to titrate a patient therapy, such as including an electrical neural modulation therapy.

In an example, such as shown in FIG. 3, a pulse transit time (PTT) can be determined. The pulse transit time can be a time interval between a triggering event and a pulse receipt event (e.g., a blood pressure pulse receipt event) in a blood vessel. In an example, a portion of the ECG signal 301 can be used as a reference to provide a PTT triggering event. The PTT triggering event can include a cardiac event, such as corresponding to a particular portion of a QRS complex. For example, a pulse transit time can be the time for an arterial pulse pressure wave to travel from a left ventricle of a heart to a peripheral body site, such as to the carotid artery. In some examples, a PTT triggering event can include the occurrence of a heart sound, or a receipt of a pulse in a first location in a blood vessel, or an emptying of the left ventricle.

In an example, such as shown in FIG. 3, a PTT triggering event can occur at a time $t_1$, or at a time when the QRS complex of a particular cardiac cycle exhibits a minimum amplitude. In an example, a PTT pulse receipt event can occur when a pulse or pressure wave arrives at or passes through a particular blood vessel location. For example, the pulse receipt event can include, among other things, a maximum arterial pressure, a threshold change in a vessel dimension, or a threshold change in a received impedance signal. In an example, such as shown in FIG. 3, a pulse receipt event can correspond to an inflection point 341 of the cervical impedance waveform 340, such as can occur at a time $t_2$. In this example, a pulse transit time can be represented by an interval $\Delta t_2$, or by an interval between $t_1$ and $t_2$. Pulse transit time, and particularly changes in pulse transit time, can be correlated with one or more physiological changes or changes in patient health status. Thus, monitoring pulse transit time can provide diagnostic information about a patient or can indicate a patient therapy, such as a neural modulation therapy.

Relative pulse pressure can be a useful parameter that can be determined, such as using impedance plethysmography analysis techniques with impedance signals obtained in a cervical region of the subject body 101. A relative pulse pressure can be conceptualized as a difference between systolic and diastolic pressures, such as relative to prior measured pressure values. In an example, such as shown in FIG. 3, a first relative pulse pressure $\Delta p_1$ can be measured using information from the cervical impedance waveform 340 as a surrogate for vessel pressure. Maxima and minima of the cervical impedance waveform 340 can correspond to maxima and minima of a vessel pressure, such as corresponding to maximum systolic and minimum diastolic pressures. A second relative pulse pressure $\Delta p_2$ can be measured at a subsequent time. In an example, a change in relative pulse pressure from $\Delta p_1$ and $\Delta p_2$ (e.g., a difference between a first measured relative pulse pressure and a second measured relative pulse pressure) can indicate a change in a patient health status. In an example, information about a relative pulse pressure can be similarly determined using the pulsatile signal waveform 330.

In an example, information about a pulse transit time or a relative pulse pressure can be used to initiate or adjust a neural modulation therapy. For example, a neural modulation therapy can be provided when a pulse transit time exceeds or falls below a predetermined threshold pulse transit time, or a neural modulation therapy can be provided when a relative pulse pressure exceeds or falls below a predetermined threshold relative pulse pressure. In an example, a combination of information about a pulse transit time or a relative pulse pressure can be used to initiate or adjust a neural modulation therapy.

In an example, a neural modulation therapy can be provided according to a first neural modulation therapy scheme 350, such as using one or more neural modulation therapy parameters to determine the characteristics of the neural modulation therapy. For example, a neural modulation therapy can be provided in coordination with a patient physiological event or patient physiological cycle. In an example, a neural modulation therapy can be provided in response to an identified pulse transit time, relative pulse pressure, or other identified physiological status indication.

In an example, a neural modulation therapy can be provided according to the first neural modulation therapy scheme 350, such as can be defined by one or more neural modulation signal characteristics. The neural modulation therapy can be provided to a neural target, such as continuously for a particular therapy delivery duration $\Delta t_n$. In an example, a discrete number of electrical neural modulation therapy signals or pulses can be provided to a neural target. In the example of FIG. 3, for example, a burst of six discrete electrical neural modulation therapy pulses can be provided, such as with an intervening delay between each pulse delivery. In an example, electrical neural modulation therapy pulses can be provided, such as after a first delay $\Delta t_{D1}$ from an identified physiological fiducial, such as corresponding to an identified patient physiological event (e.g., a pulsatile signal waveform peak event) or patient physiological cycle (e.g., a pulsatile signal waveform cycle).

Figure 4:
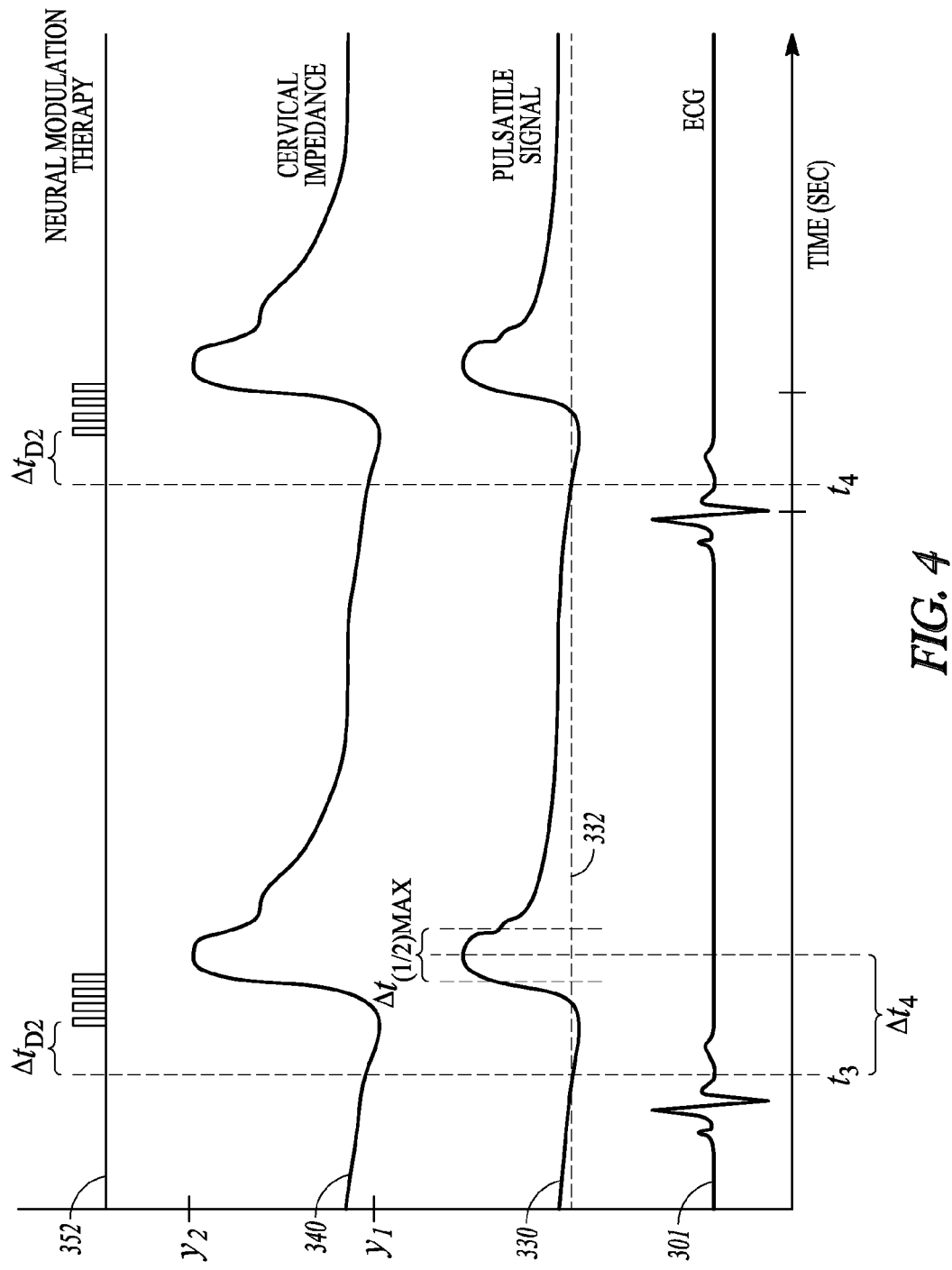
FIG. 4 illustrates generally an example of an ECG waveform with a corresponding cervical impedance waveform, a corresponding pulsatile signal waveform, and a neural modulation therapy scheme.

In an example, a number, or quantity, of neural modulation therapy pulses can be adjusted, such as according to a neural modulation therapy parameter. For example, FIG. 4 illustrates generally a second neural modulation therapy scheme 352, such as comprising a burst of four discrete electrical neural modulation therapy pulses, such as with an intervening delay between each pulse delivery (e.g., the intervening delay can be the same or different than the intervening delay in the example of the first neural modulation therapy scheme 350). The number of discrete electrical neural modulation therapy pulses in the neural modulation therapy scheme can be adjusted to be zero or more, such as according to a neural modulation therapy parameter.

In an example, a delay preceding a neural modulation therapy delivery scheme can be adjusted, such as according to a neural modulation therapy parameter. FIG. 4 illustrates generally a second delay, $\Delta t_{D2}$, such as extending from an identified physiological fiducial (e.g., at $t_3$ or $t_4$) to an initial delivery of a neural modulation therapy pulse. The delay can be adjusted to be zero or more, such as according to a neural modulation therapy parameter.

Referring to FIG. 3 or FIG. 4, an amplitude of a portion of the pulsatile signal waveform 330 can be used to adjust a neural modulation therapy parameter or initiate a neural modulation therapy. For example, a peak amplitude 331 of the pulsatile signal waveform 330, such as an absolute peak during a particular time window, or a relative peak, such as relative to one or more of a predetermined threshold, a previously-observed minimum, or a previously-observed maximum of the pulsatile signal waveform 330, can be used to indicate a neural modulation therapy. That is, upon detection of a peak of the pulsatile signal waveform 330, such as by the processor circuit 110, a neural modulation therapy parameter can optionally be determined, or an electrical neural modulation therapy (e.g., comprising one or more neural modulation therapy pulses) can be provided to a neural target (e.g., a cervical neural target) using the electrical energy delivery circuit 220 and the neural modulation therapy parameter.

In an example, an electrical neural modulation therapy can be provided, such as in continuous burst fashion, while an amplitude of a portion of the pulsatile signal waveform 330 exceeds a predetermined threshold amplitude. For example, the electrical neural modulation therapy can be initiated in response to a first identified characteristic of the pulsatile signal waveform 330 (e.g., as the waveform exceeds a predetermined threshold amplitude), and the electrical neural modulation therapy can be terminated in response to a second, subsequently identified characteristic of the pulsatile signal waveform 330 (e.g., as the waveform falls below the predetermined threshold amplitude).

In an example, a timing characteristic of a portion of the pulsatile signal waveform 330 can be used to initiate or adjust a neural modulation therapy. For example, a timing of a portion of the pulsatile signal waveform 330 can include a time indicative of a particular characteristic of the pulsatile signal waveform 330, such as a time indicative of a pulsatile signal waveform peak, a pulsatile signal waveform inflection point, a pulsatile signal waveform minimum, or a time indicative of some other characteristic of the pulsatile signal waveform. A timing characteristic of a portion of the pulsatile signal waveform 330 can include a duration, such as corresponding to an interval between an identified first characteristic of the pulsatile signal waveform 330 (e.g., an identified peak, inflection point, relative minimum or maximum, etc.) and some other, subsequently identified waveform characteristic or event, such as corresponding to the pulsatile signal waveform 330 or another waveform. For example, a timing of a portion of the pulsatile signal waveform 330 can include an interval between an identified relative peak of the pulsatile signal waveform 330 and a characteristic of the ECG waveform 601, such as an R-wave peak (e.g., the interval $\Delta t_1$ illustrated in FIG. 3). The interval can be compared to a threshold interval and, when the duration exceeds or falls below a particular threshold duration, a neural modulation therapy can be initiated, such as according to the neural modulation therapy scheme 350, such as using the processor circuit 110. In an example, a timing of a portion of the pulsatile signal waveform 330 can include an interval between identified peaks of the pulsatile signal waveform 330, such as corresponding to adjacent cardiac cycles (e.g., the interval $\Delta t_3$ illustrated in FIG. 3).

In an example, a timing of a portion of the pulsatile signal waveform 330 can include an interval between a pulsatile signal waveform 330 threshold crossing (e.g., in the example of FIG. 4, a point at which the pulsatile signal waveform 330 crosses a pulsatile signal threshold 332) and a pulsatile signal waveform 330 relative maximum. In an example, the interval can be compared to a threshold interval, such as to indicate a neural modulation therapy, or to adjust a neural modulation therapy parameter. Other timings of the pulsatile signal waveform 330, such as in coordination with one or more of the cervical impedance waveform 340, the ECG waveform 301, or other indications of physiological patient activity, can be used.

In an example, a frequency of a portion of the pulsatile signal waveform 330 can be used to adjust a neural modulation therapy parameter or initiate a neural modulation therapy. For example, changes in a frequency of the pulsatile signal waveform 330, such as can be determined using the processor circuit 110, can be used to suppress or indicate a neural modulation therapy. In an example, a frequency change can indicate an adjustment of a neural modulation therapy parameter.

In an example, an increasing frequency of the pulsatile signal waveform 330 can indicate an increasing patient heart rate. In response to the increased frequency, a neural modulation therapy parameter can be adjusted, such as corresponding to one or more neural modulation therapy pulse characteristics, such as an increased pulse amplitude or increased pulse delivery frequency. In an example, a frequency of other characteristics of the pulsatile signal waveform 330 can be monitored or trended, such as to provide information about a patient health status or trend. For example, a frequency of threshold amplitude crossings of the pulsatile signal waveform 330 can be monitored or trended.

In an example, a shape of a portion of the pulsatile signal waveform 330 can be used to adjust a neural modulation therapy parameter or initiate a neural modulation therapy. For example, a slope of a portion of the pulsatile signal waveform 330 can be used. In an example, a decreasing slope, such as decreasing at a particular rate, can correspond to a first neural modulation therapy parameter, and an increasing slope, such as increasing at a particular rate, can correspond to a different second neural modulation therapy parameter. Other indications of shape of the pulsatile signal waveform 330 can be used. For example, width of a pulsatile signal waveform peak can be assessed, such as by the processor circuit 110, to adjust or initiate a neural modulation therapy.

In an example, an integral of a portion of the pulsatile signal waveform 330 can be used to adjust a neural modulation therapy parameter or initiate a neural modulation therapy. For example, an integral of a portion of the pulsatile signal waveform 330 can be used as an indication of a shape of the pulsatile signal waveform 330, such as can provide information about an area below or above a portion of the pulsatile signal waveform 330 curve. The area information can be used, such as by the processor circuit 110, to adjust or initiate a neural modulation therapy. Similarly, a derivative of a portion of the pulsatile signal waveform 330 can be used to initiate or adjust a neural modulation therapy.

In an example, a sum, difference, linear combination, ratio, or product of characteristics, such as of the pulsatile signal waveform 330 described above, among other characteristics of the various waveforms or other features indicative of patient physiological activity, can be used to adjust a neural modulation therapy parameter or initiate a neural modulation therapy. For example, information about a difference or sum of adjacent peak magnitudes of the pulsatile signal waveform 330 can be used to adjust or initiate a neural modulation therapy.

In an example where the IMD 105 includes a CRM component or is communicatively coupled to a CRM device, information from any one or more of the ECG waveform 301, the pulsatile signal waveform 330, or the cervical impedance waveform 340 can be used to initiate or adjust a CRM therapy. For example, any of the characteristics of the pulsatile signal waveform 330 or the cervical impedance waveform 340, among others, can be used to trigger CRM or neural modulation therapies, or both. In an example, a characteristic of the cervical impedance waveform 340 (e.g., a frequency characteristic of the cervical impedance waveform 340) can be used to initiate or adjust a bradycardia or anti-tachycardia therapy.

Figure 5:
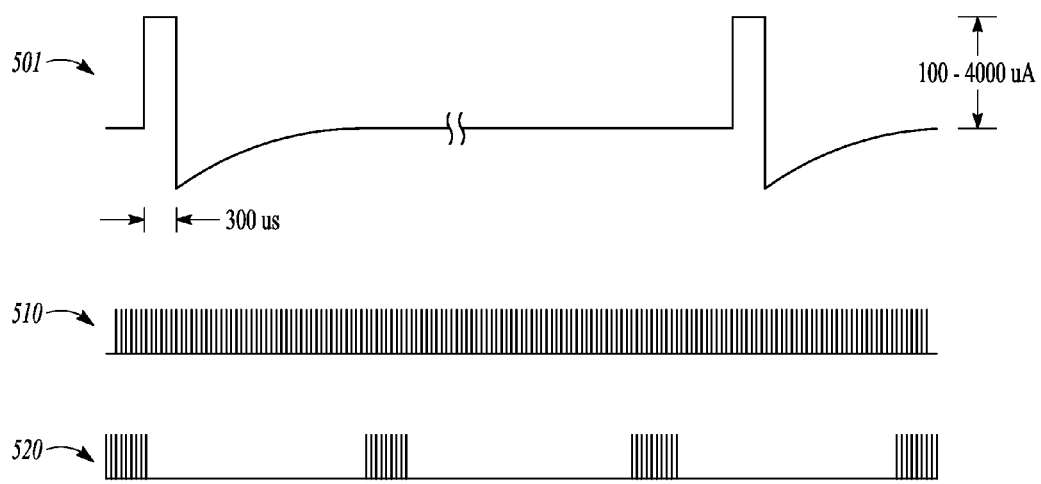
FIG. 5 illustrates generally an example that can include a neural stimulation therapy pulse.

A neural modulation therapy can be provided to a neural target using an electrical neural modulation therapy signal. An electrical neural modulation therapy signal can be defined by multiple signal characteristics, including amplitude, frequency, shape, duration, DC offset, timing, delay, or number of phases, among other characteristics. FIG. 5 illustrates generally an example of a biphasic electrical neural modulation therapy signal 501, such as comprising two neural modulation therapy pulses. In an example, the neural modulation therapy signal 501 can be provided to, among other locations, a cervical region of the subject body 101.

The neural modulation therapy signal 501 can be provided according to one or more neural modulation therapy parameters that can be used to determine or define one or more characteristics of the neural modulation therapy signal 501. For example, using a neural modulation therapy parameter, the processor circuit 110 can instruct the electrical energy delivery circuit 220 to provide a neural modulation therapy signal having particular signal characteristics (e.g., particular signal characteristics such as a particular amplitude, duration, or timing, etc.).

In an example, the neural modulation therapy signal 501 can include a biphasic pulse signal having a first, positive phase duration of about 300 µs at an amplitude of about 100-4000 µA. The neural modulation therapy signal 501 can include a second, negative phase, such as following the first phase and having an initial minimum magnitude less than zero. The second, negative phase can include a positively sloped portion, extending from the initial minimum, such as continuously or exponentially increasing toward zero.

In an example, the neural modulation therapy signal 501 can be delivered to the subject body 101 substantially continuously, such as at a pulse frequency of about 20 Hz. At 510, FIG. 5 illustrates generally a graphical representation of such a continuous delivery of the neural modulation therapy signal 501.

In another example, the neural modulation therapy signal 501 can be delivered to the subject body 101 in burst fashion. For example, the neural stimulation signal can be delivered intermittently, such as by delivering a train or burst of neural modulation therapy pulses for about 10 seconds, pausing for about 50 seconds, and resuming delivering the signal for a subsequent 10 second burst. During the about 10 seconds that the neural modulation therapy pulses are applied, the pulses can be applied at a pulse frequency of about 20 Hz. The intermittent neural stimulation may be delivered according to a programmed schedule that may be used to control start times, or stop times, or duration of the pulse trains, or combinations thereof. Programmed intermittent neural stimulation therapies may be used to treat chronic conditions such as heart failure and hypertension. At 520, FIG. 5 illustrates generally a graphical representation of such discontinuous, or burst, delivery of the neural modulation therapy signal 501.

In an example, a neural modulation therapy pulse can be used to deliver a patient therapy and to deliver a test electrical signal to a patient body, such as an impedance measurement pulse. In an example, some neural modulation therapy pulse characteristics can be common to impedance measurement pulses (e.g., non-neurostimulating pulses) and neural modulation therapy pulses, such as vagus nerve stimulation (VNS) pulses. In an example, both neurostimulating and non-neurostimulating signals can include at least some similar pulse characteristics, such as similar amplitude, similar pulse width, or similar frequency. This overlap in pulse signal characteristics, such as in combination with an appropriate electrode location configuration, can enable dual use of the impedance measurement and neural stimulation pulses, such as to provide neural modulation therapy or to evoke an impedance measurement response signal using the neural modulation therapy pulse energy as an "excitation" or "test" energy for obtaining the impedance information.

One or several benefits, such as including improved signal to noise performance and noise rejection, can be obtained by using neural modulation therapy pulses as pulses for impedance measurements. In an example, a neural modulation therapy pulse can be delivered at a relatively high current level that exceeds a nerve tissue capture threshold. In contrast, pulses used exclusively for impedance measurements can be delivered at relatively low, non-tissue stimulating current levels. By using a higher-amplitude neural modulation therapy pulse as at least a portion of an impedance measurement pulse, a functional impedance measurement response signal can be more likely to be received, and concerns about tissue capture during impedance measurement can be reduced or eliminated. In addition, using a relatively high amplitude therapy pulse as an impedance measurement pulse can provide better resolution of the responsive or received measurement signals. For example, a signal to noise ratio of an impedance measurement-only response signal relative to background electrical noise can be improved. Because of the higher amplitude, there can be reduced susceptibility to interference, both internally to the subject body 101 and externally.

In addition, combining therapy pulses and impedance measurement pulses can improve the longevity of a medical device, such as by reducing power consumption requirements by consolidating the number of individual pulses that are delivered to the subject body. In addition, by using neural stimulation signals as impedance plethysmography pulses, overall system design can be facilitated or other trade-offs can advantageously be made because there is little or no need to avoid collisions between neural stimulation pulses and impedance plethysmography pulses.

Figure 6:
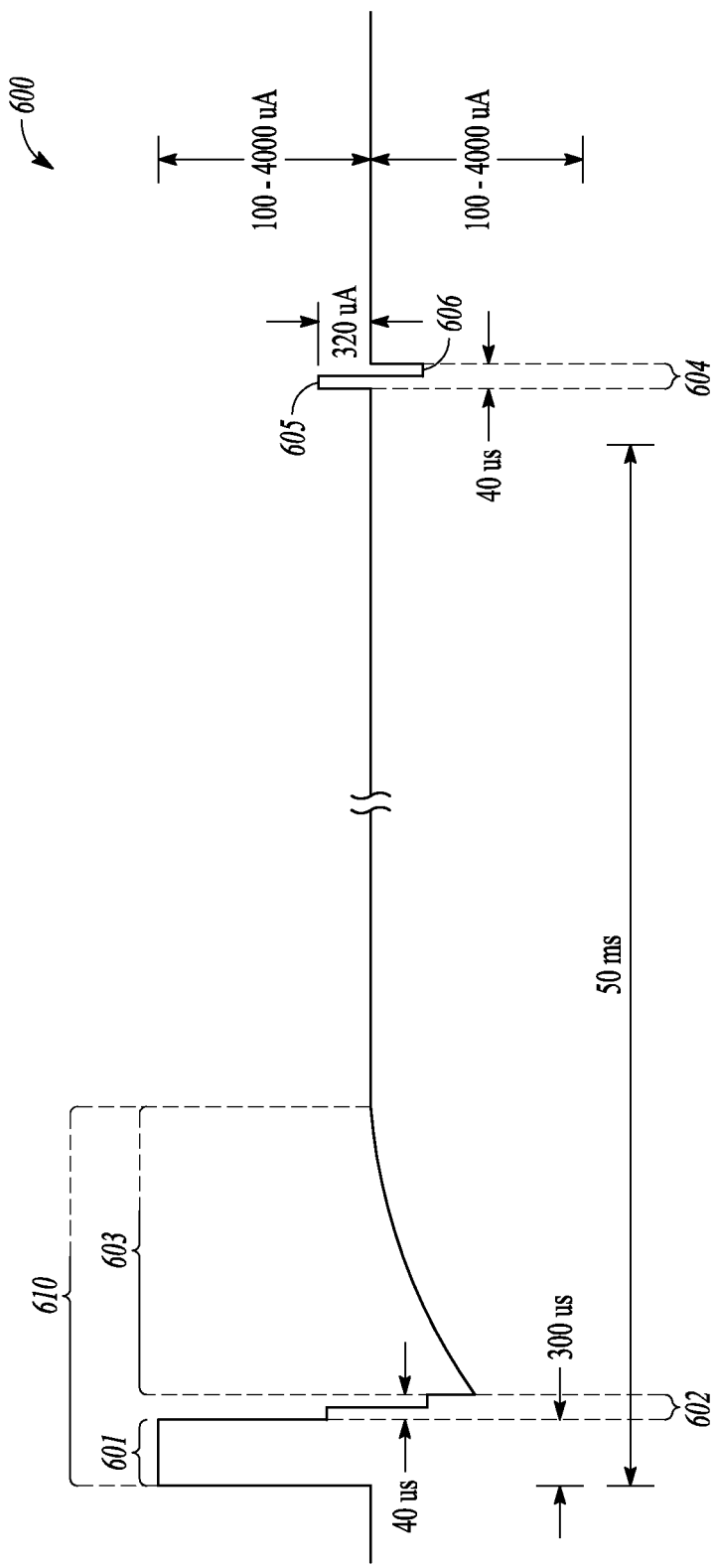
FIG. 6 illustrates generally an example that can include a neural stimulation therapy pulse that includes an impedance plethysmography signal component.

FIG. 6 illustrates generally an example that can include a pulse that includes neural stimulation and impedance plethysmography components. A pulse waveform 600 can include at least a first composite pulse component 610. The illustrated first composite pulse component 610 includes a neural stimulation positive phase pulse component 601, an impedance plethysmography pulse component 602, and a neural stimulation negative phase pulse component 603. The pulse waveform 600 can include a second pulse component 604. The illustrated second pulse component 604 includes a positive phase 605 and a negative phase 606 of an impedance plethysmography pulse, such as can be used to evoke an electrical response that can be used to measure impedance.

In an example, such as shown in FIG. 6, an impedance plethysmography pulse can be appended to a trailing portion of the neural stimulation positive phase pulse component 601. This configuration can help improve repeatability of impedance plethysmography measurements at least because a consistent amplitude for the impedance plethysmography pulse (e.g., about 320 μnA peak) can be used regardless of an amplitude of the neural stimulation pulse signal.

In an example, one or a series of impedance measurement pulses may be delivered when neural modulation therapy is not being delivered. During these "off" portions of a neural modulation therapy pulse train, impedance plethysmography pulses (e.g., non-tissue-stimulating pulses) can be provided to the subject body 101 to obtain impedance measurements. A responsive impedance signal can be used to identify phases of a blood pressure cycle (e.g. systole and diastole). The timing of one or both of these phases can be used to control the timing of the neural stimulation therapy. For example, the neural stimulation therapy may be used to elicit a baroreflex response that mimics or augments a natural baroreflex response induced by the baroreceptor response to pulsating blood flow.

In an example, dimensional changes of a blood vessel can be correlated with changes in a patient pulse pressure. For example, when a pulse or blood surge passes through a vessel, the vessel can expand as the pressure exerted by the blood acts upon the vessel walls. In an example, expansion or contraction of a cervical blood vessel can be determined using a cervical impedance signal, such as after a cervical impedance measurement response signal is filtered or otherwise processed to identify the signal components of interest. For example, the processor circuit 110 can be configured to receive an impedance measurement response signal, such as via the detector circuit 222, and can be configured to determine impedance measurement response signal components representative of a pulse pressure. In an example, a decrease in an amplitude of a cervical impedance signal can indicate a full or expanded cervical blood vessel. In an example, information about a blood vessel dimensional change can be used as a surrogate for information about baroreceptor activity.

In an example, such as shown in FIG. 6 at 604, an impedance measurement pulse can include a biphasic current pulse having a pulse duration of about 40 μs and a peak amplitude of about 80 to 320 μA. In an example, the impedance measurement pulse can be delivered to the subject body 101 about every 50 ms such that an impedance measurement response signal can be continuously or recurrently sampled at about 20 Hz. Continuously or recurrently sampled impedance measurement response signals can be used to provide impedance response information over time.

Figure 7A:
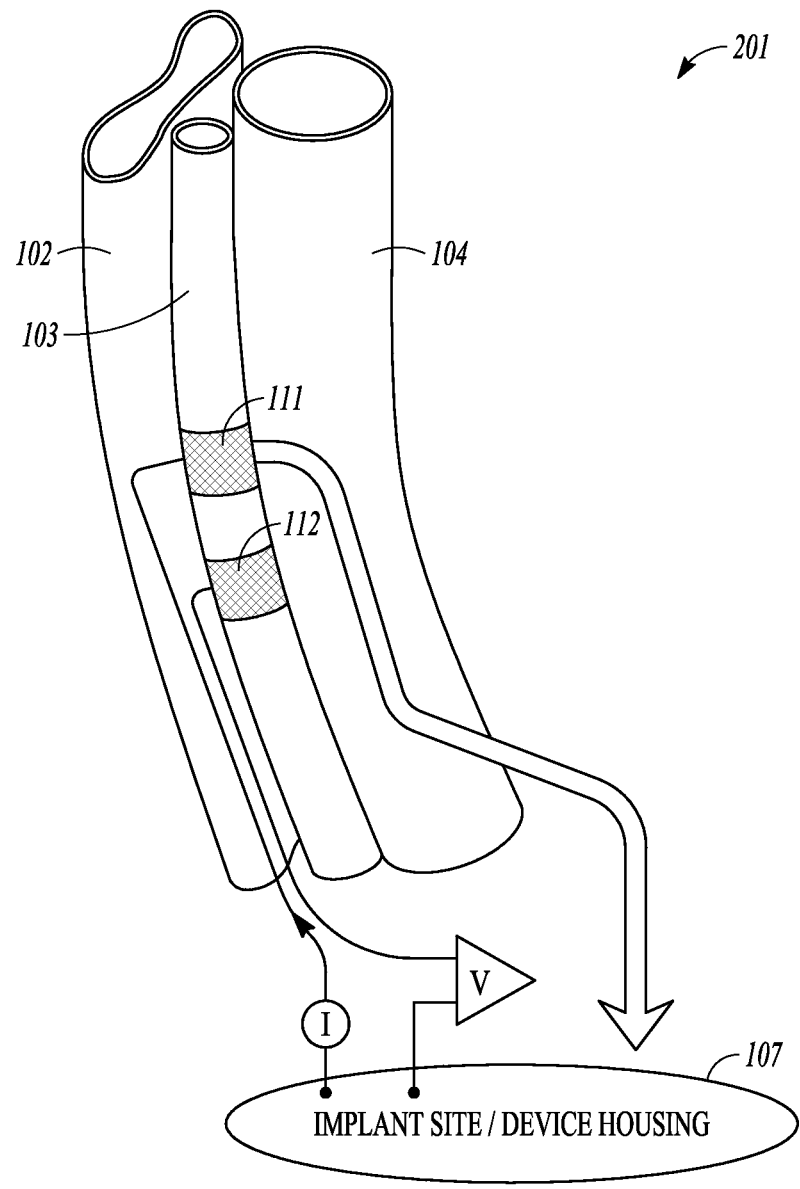
FIG. 7A illustrates generally an example that can include a unipolar energy delivery or sensing system.
Figure 7B:
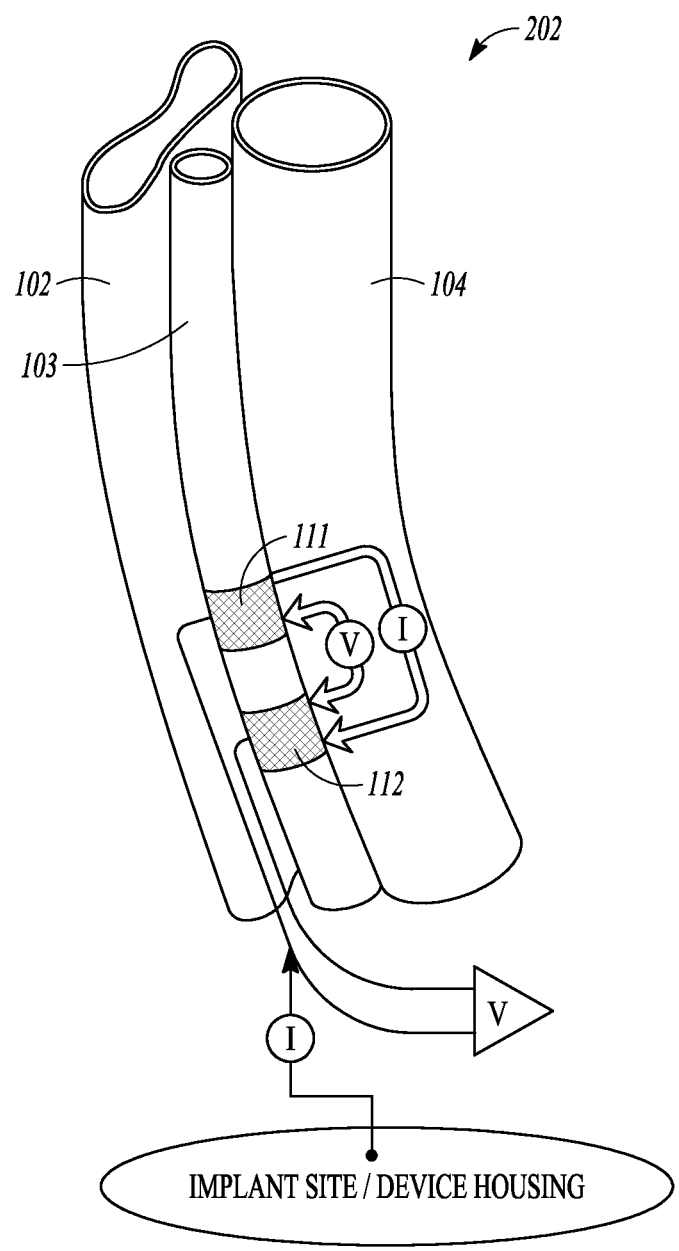
FIG. 7B illustrates generally an example that can include a bipolar energy delivery or sensing system.

Unipolar and bipolar electrode configurations can be used to provide an impedance measurement pulse, to provide electrical neural modulation therapy, or to receive responsive electrical signals, such as an impedance signal. FIG. 7A illustrates generally an example of unipolar measurement and therapy delivery configurations, and FIG. 7B illustrates generally bipolar measurement and therapy delivery configurations. Some embodiments use a unipolar measurement configuration and a bipolar therapy delivery configuration, and some embodiments use a unipolar therapy delivery configuration and a bipolar measurement configuration.

The embodiments illustrated generally in FIGS. 7A and 7B can be used to acquire an impedance signal, such as using one or more electrodes disposed within the body (e.g., using the first and second electrodes 111, 112, such as disposed near a vagus nerve 103). Characteristics of the impedance signal can be used to control a neural stimulation therapy. The impedance signal may also be used to manage or monitor a therapy or a condition of the patient, such as heart failure status.

In an example, an acquired impedance signal can be interpreted or processed using one or more plethysmography techniques, such as using the processor circuit 110 to interpret a relatively small change in electrical impedance in a body and, in response, provide a neural modulation therapy. An impedance signal for plethysmography analysis can be obtained using one or more electrodes that can be disposed in, among other locations, a cervical region of the patient body 101, such as using one or more cuff electrodes that can be disposed at or around the vagus nerve 103. In an example, impedance plethysmography can be used to determine a change in a blood vessel dimension (e.g., a change in a dimension of the carotid artery 104), such as a change in a cross-sectional area or a radial dimension. In an example, impedance plethysmography can be used to determine, among other things, pulsatile motion of a blood vessel, blood flow, or blood pressure.

FIG. 7A illustrates generally an example of a system 201 that can be configured to provide a unipolar electrical signal to the subject body 101. For example, the processor circuit 110 can initiate an electrical current pulse that can be provided along the current path I illustrated in FIG. 7A (e.g., an impedance measurement pulse, such as can be used to evoke an impedance response, or an electrical therapy pulse, such as can be used to provide a neural modulation therapy). The electrical energy delivery circuit 220 can be configured to deliver the current pulse using the first electrode 111, such as to deliver the current pulse to a neural stimulation target location proximate to the vagus nerve 103.

In the example of FIG. 7A, the system 201 can be configured to receive an impedance measurement response signal, such as in response to the electrical current pulse. The impedance measurement response signal can be received across a cervical or thoracic region of the subject body 101. For example, the detector circuit 222 can be configured to measure a thoracic impedance measurement response signal by receiving an electrical response signal (e.g., using a voltage signal, denoted in FIG. 7A by the voltage measurement circuit V) using the conductive housing 107 and at least one of the first electrode 111 or the second electrode 112, such as when the conductive housing 107 is disposed in the thorax of the subject 101.

FIG. 7B illustrates generally an example of a system 202 that can be configured to provide a bipolar electrical stimulation signal to a cervical region in the patient body 101, such as at or near the vagus nerve 103. For example, the bipolar configuration of the system 202 can be used to provide a focused delivery of electrical energy to a region in the subject body 101 (e.g., a cervical region). For example, the electrical energy delivery circuit 220 can be configured to deliver a current pulse to a target cervical location using multiple electrodes disposed at or near the target location, such as using the first electrode 111 and the second electrode 112. In the example of FIG. 7B, a current path is denoted I.

The system 202 can be configured to receive an impedance measurement response signal, such as a voltage signal obtained across a cervical region of the subject body 101. For example, the detector circuit 222 can be configured to measure a cervical impedance by receiving an impedance measurement response signal using the first electrode 111 and the second electrode 112, such as when the first and second electrodes are disposed in the cervical region. In the example of FIG. 7B, the electrical response signal can include a voltage signal detected by the voltage measurement circuit V, such as including a voltage between the first and second electrodes 111 and 112.

In an example, the first electrode 111 and the second electrode 112 can be electrodes disposed on a single implantable lead, such as a multipolar electrode lead comprising two or more electrodes. For example, the first electrode 111 and the second electrode 112 can be two of four electrodes on a quadripolar electrode lead. In an example, the same or different electrodes can be used to deliver a current pulse or to receive a corresponding, responsive voltage signal. Illustrative examples of electrode configurations for performing impedance measurements are described in Stahmann et al., U.S. Pat. No. 7,387,610, entitled THORACIC IMPEDANCE DETECTION WITH BLOOD RESISTIVITY COMPENSATION, which is incorporated herein by reference in its entirety.

In an example, the processor circuit 110 can execute an electrode selection algorithm to select appropriate electrodes for delivering electrical pulses or receiving electrical response signals. For example, the first electrode 111 or the second electrode 112 can be selected from among three or more available electrodes, such as disposed on any one or more implantable leads in the implantable lead system 108, on the IMD 105, or elsewhere. In an example, an electrode selection algorithm can analyze one or more electrode selection parameters, such as impedance signal strength or repeatability, such as using available pairs or combinations of electrodes. The electrode selection parameters can then be used to select electrodes for energy delivery or measurement.

Figure 8:
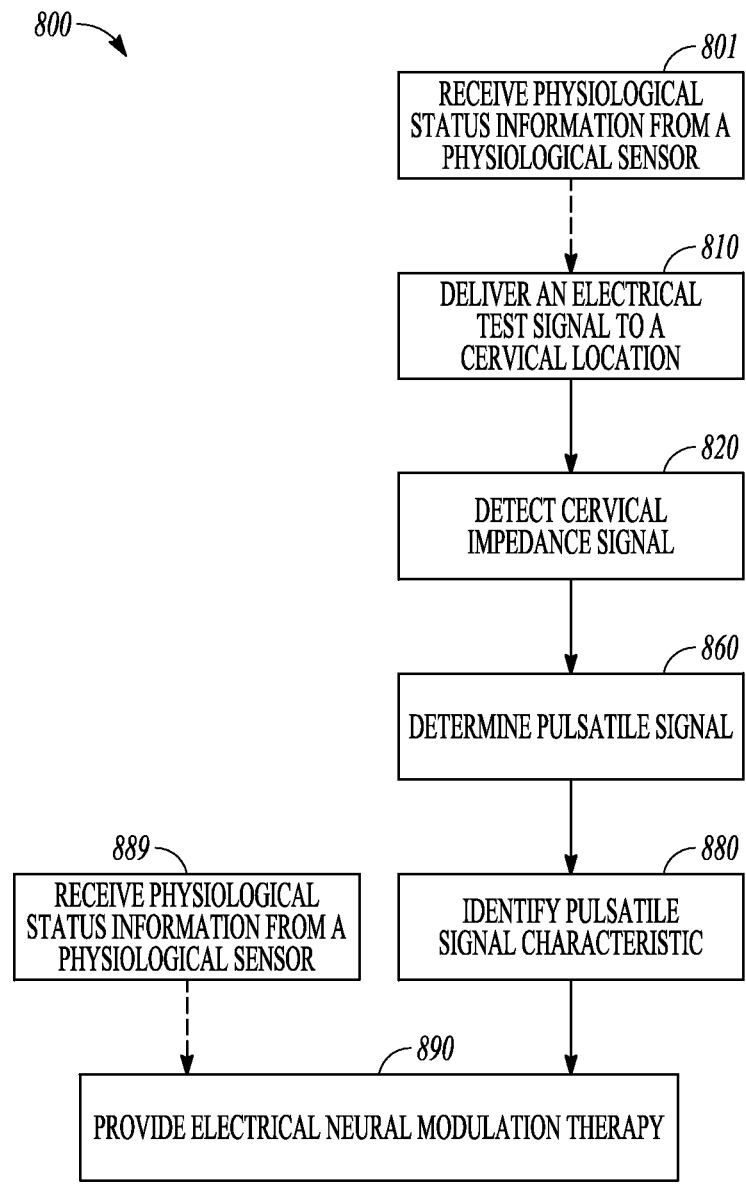
FIG. 8 illustrates generally an example that can include providing an electrical neural modulation therapy.

FIG. 8 illustrates generally an example that can include providing an electrical neural modulation therapy. At 810, an electrical test signal can be provided internally within a patient body, such as using one or more of the systems 100, 201, or 202, among others. For example, the electrical test signal can be a non-tissue stimulating (e.g., sub-capture threshold) signal, such as comprising one or more electrical test pulses, such as impedance measurement plethysmography pulses. The electrical test signal can include a tissue stimulating signal, such as a neural modulation therapy signal, such as configured to provide an autonomic modulation therapy to a patient nerve. In an example, the electrical test signal can be delivered to a cervical region within a subject body 101, such as at or near the vagus nerve 103 and proximal to the carotid artery 104.

At 820, a cervical impedance signal can be detected, such as using the detector circuit 222. In an example, the cervical impedance signal can be detected or received in response to the electrical test signal provided at 810. In an example, the cervical impedance signal can be analyzed as an impedance plethysmography signal, such as using the processor circuit 110, or stored using a processor-readable medium coupled to the processor circuit 110.

At 860, a pulsatile signal can be determined, such as using the detected cervical impedance signal. In an example, a cervical impedance signal can be filtered, analyzed, or otherwise processed to determine a pulsatile signal, such as a signal indicative of fluctuations in a carotid artery pulse pressure. In some cases, particular frequency components (e.g., frequency components determined experimentally or components that are unique to a particular patient) can be eliminated from a cervical impedance signal to acquire an accurate pulsatile signal. As shown generally in FIG. 3, for example, a pulsatile signal (e.g., the pulsatile signal waveform 330) can correspond generally to a cervical impedance signal. For example, an inflection point characteristic of the pulsatile signal waveform 330 can temporally correspond with an inflection point characteristic of the cervical impedance waveform 340, or a variable interval can exist between the inflection point characteristics. In an example, the variable interval between the inflection point characteristics can include useful information about a patient physiological status, such as can be used to initiate or adjust a neural modulation therapy.

In an example, the pulsatile signal determined at 860 can be a function of a vessel dimension, such as can be determined using the detected cervical impedance signal as an impedance plethysmography signal. Using impedance plethysmography, a value of a detected impedance change can be correlated with a change in a blood vessel volume or a change in a blood vessel dimension. In an example, a vessel dimension can be determined by analyzing differences in the detected cervical impedance signal, including differences in amplitude, phase, or other features or characteristics of the impedance signal. In an example, the determined vessel dimension can be a radial blood vessel dimension (e.g., a radial dimension of a carotid artery), changes in which can be correlated to changes in pulse pressure.

At 880, a pulsatile signal characteristic can be identified. As shown generally in FIGS. 3 and 4, a pulsatile signal (e.g., the pulsatile signal waveform 330) can include numerous characteristics or features. For example, pulsatile signal characteristics can include, among others, a timing of a portion of the pulsatile signal, an amplitude of the pulsatile signal, a frequency determined using the pulsatile signal, a shape of the pulsatile signal, an integral of the pulsatile signal, a derivative of a portion of the pulsatile signal, or a ratio, sum, difference, linear combination, or product of characteristics of the pulsatile signal or another physiological signal, such as described above in the discussion of FIGS. 3 and 4. In an example, a pulsatile signal characteristic can include a composite characteristic, such as including information about one or more characteristics of other physiological signals. For example, a pulsatile signal characteristic can include information about a characteristic of a pulse pressure signal (e.g., a peak pulse pressure) and information about a characteristic of a corresponding ECG signal (e.g., an amplitude of the ECG signal at the time of the peak pulse pressure, or an interval between an ECG signal characteristic and the peak pulse pressure). In an example, at 880, an identified pulsatile signal characteristic can include a comparison of one or more pulsatile signal characteristics with a predefined threshold, or a comparison with previously acquired, patient-specific pulsatile signal characteristic information.

In an example, the processor circuit 110 can be configured to determine a reference pulsatile signal characteristic during a device learning period. The learning period can include multiple physiological cycles, such as corresponding to one or more patient physical activity levels. In an example, a reference pulsatile signal characteristic can be determined using information obtained while a patient is at rest, such as over multiple cardiac cycles, such as including averaged signal characteristic information. The pulsatile characteristic information can be measured at about the same time during or after a cardiac contraction, such as for each of the multiple cardiac cycles.

At 890, an electrical neural modulation therapy can be provided. In an example, the electrical neural modulation therapy can be provided using the system 100, 201, or 202, among others, such as using one or more electrical neural modulation therapy parameters to define the therapy. In an example, the pulsatile signal characteristic identified at 880 can be used to provide the electrical neural modulation therapy at 890. For example, the pulsatile signal characteristic identified at 880 can be used to time delivery of the electrical neural modulation therapy, such as by providing a fiducial reference point from which to begin a neural modulation therapy scheme (e.g., the first neural modulation therapy scheme 350, among other schemes).

In an example, such as shown in FIG. 8 at 801 or 889, physiological status information can be received from a physiological sensor (e.g., the physiological sensor 204). In an example, physiological status information can be received in response to a change in a patient physiological status. For example, the received information can indicate a change in, among other things, one or more of a patient activity level, a patient posture, a heart rate or respiratory rate, an intrinsic neural activity level, or an arrhythmia status.

In an example, at 801, information about a patient physiological status can be received from the physiological sensor 204. Upon receipt of the information, the processor circuit 110 can initiate delivery of the electrical test signal at 810. Similarly, at 889, the processor circuit 110 can receive physiological information from the same or a different physiological sensor. In response to receiving the physiological information, the processor circuit 110 can, at 890, initiate a calculation, diagnostic procedure, or therapy, such as an electrical neural modulation therapy.

In an example, the information about the patient physiological status received at 801 or 889 can include patient physical activity status information, such as including information from an accelerometer circuit, such as can be included in the system 100. In an example, the received patient physiological status information can include impedance information, such as thoracic or cervical impedance information, such as can be used to determine a patient respiratory status. In an example, the received information can include a blend of impedance information and information from an accelerometer, such as to provide a comprehensive signal indicative of a patient's metabolic demand. In an example, the comprehensive signal indicative of metabolic demand can be used, such as together with patient pulsatile information, to determine one or more neural modulation therapy parameters, such as can be used at 890 to time delivery of an electrical neural modulation therapy.

In an example, the information about the patient physiological status received at 801 or 889 can include intrinsic neural activity information. For example, an intrinsic neural activity signal can be detected, such as using one or more electrodes disposed at or near nerve tissue. In an example, intrinsic neural activity information can be inferred, such as using a patient physiological activity signal, such as a pulsatile signal or a baroreceptor activity signal. In an example, an intrinsic parasympathetic surge can occur in coordination with a peak of a pulsatile signal waveform. At 890, an electrical neural modulation therapy can be provided, such as in coordination with the detected intrinsic neural activity to augment a patient's intrinsic neural activity, such as to augment an intrinsic parasympathetic surge. In an example, a characteristic of the intrinsic neural activity signal can be used to trigger or adjust a neural modulation therapy parameter.

In an example, information about other activity of the IMD 105 can be used to indicate or adjust a neural modulation therapy parameter. For example, the processor circuit 110 can be configured to time delivery of an electrical neural modulation therapy in coordination with a refractory period, or blanking period, of a portion of the IMD 105. In an example, the IMD 105 can be configured to deliver electrostimulation to cardiac muscle tissue. During a blanking period when the IMD 105 is not delivering electrostimulation to the cardiac muscle tissue (e.g., during a cardiac refractory period), the IMD 105 can be configured to provide the electrical neural modulation therapy. In an example, coordinating delivery of a neural modulation therapy with a blanking period of the IMD 105 can help avoid a therapy collision, or can help avoid artifacts, such as within a patient body, that a portion of the IMD 105 may view as unusual or unexpected physiological behavior.

Figure 9:
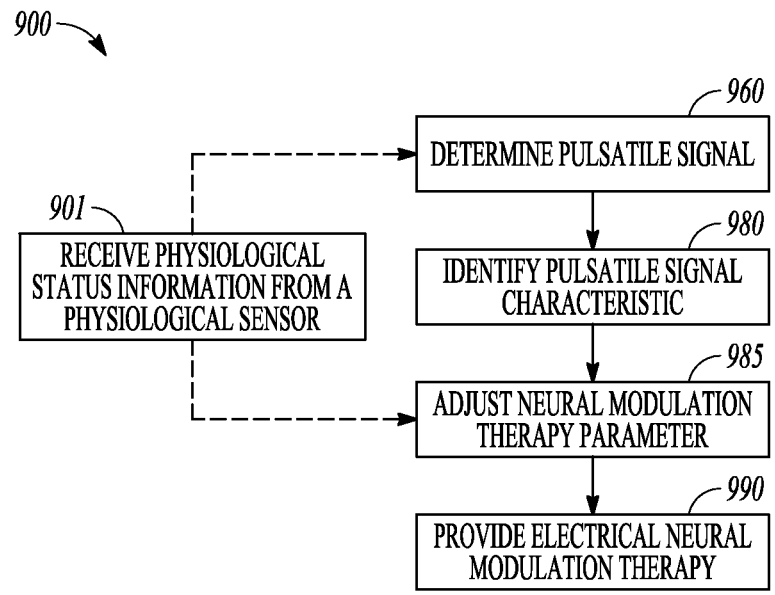
FIG. 9 illustrates generally an example that can include adjusting a neural modulation therapy parameter.

FIG. 9 illustrates generally an example that can include adjusting a neural modulation therapy parameter or providing an electrical neural modulation therapy. In an example, at 960, a pulsatile signal can be determined, such as according to the discussion at 860. At 980, one or more pulsatile signal characteristics can be identified, such as according to the discussion at 880. At 985, one or more neural modulation therapy parameters can be adjusted. For example, one or more neural modulation therapy parameters can be adjusted using information about a pulsatile signal characteristic identified at 980. Among other places in this document, adjusting a neural modulation therapy parameter is described above, such as in the discussion of FIG. 3 or FIG. 4. In an example, a neural modulation therapy timing parameter can be adjusted at 985 using information about the pulsatile signal characteristic identified at 980. For example, a therapy delay time can be eliminated such that, at 990, an electrical neural modulation therapy can be provided as soon as possible after identification of a particular pulsatile signal characteristic at 980 by the processor circuit 110.

In an example, at 985, a neural modulation therapy parameter, such as can be used to determine an amplitude, frequency, duration, timing, or other characteristic of a neural modulation therapy pulse, can be adjusted using the processor circuit 110, such as in response to one or more pulsatile signal characteristics identified at 980. In an example, at 990, an electrical neural modulation therapy can be provided, such as to a neural target, using the adjusted neural modulation therapy parameter.

At 901, physiological status information can be received from a physiological sensor, such as the physiological sensor 204. In an example, the physiological status information can be received according to the discussion at 801 or 889. In an example, at 985, the received physiological status information can be used to adjust a neural modulation therapy parameter. In an example, at 985, at least one of the received physiological status information or the identified pulsatile signal characteristic (e.g., identified at 980) can be used to adjust a neural modulation therapy parameter.

In an example, at 901, the received physiological status information can include information about a patient posture status. The posture information can be used, such as together with a pulsatile signal characteristic, to time delivery of a neural modulation therapy at 990. In an example, the processor circuit 110 can receive the posture information and can correspondingly adjust one or more neural modulation therapy parameters.

In an example, posture information, such as can be received at 901, can be used to determine the pulsatile signal at 960. Patient posture can have an effect on blood vessels, such as cervical blood vessels, which can change shape (e.g., such as can significantly collapse or distend) in response to a patient posture change. Accordingly, cervical impedance measurements can vary widely depending on patient posture, such as when a patient is upright or lying down. In an example, a cervical blood vessel can become engorged, such as when a patient lies down. Because of the engorgement, when the patient is lying down, the patient's cervical impedance can be substantially lower than when the patient is upright. Accordingly, at 960, the processor circuit 110 can compensate for such cervical impedance changes by adjusting a baseline cervical impedance or by adjusting a pulsatile signal waveform.

In an example, posture information, such as can be received at 901, can be used to initiate, terminate, or adjust a neural modulation therapy. For example, a particular neural modulation therapy (e.g., a neural modulation therapy defined at least in part by a particular neural modulation therapy parameter) can be configured to be delivered when a patient is at rest or sleeping. The processor circuit 110 can use posture information to detect when the patient is lying down for an extended period of time, and, when detected, the processor circuit 110 can initiate or adjust a neural modulation therapy.

In an example, the pulsatile signal determined at 960, such as using the physiological information received at 901, can be used to provide other patient health status information, such as can be used to determine one or more neural modulation therapy parameters. For example, a change in a patient pulsatile signal, such as with or without a corresponding change in the received physiological status information, can indicate a change in a patient health status. For example, a patient health status change can be indicated when a reduction in a pulsatile signal amplitude occurs in the absence of a corresponding change in the patient's posture (e.g., determined using physiological posture information received at 901). In an example, an electrical neural modulation therapy can be provided in response to a patient health status change.

A neural modulation therapy parameter can be adjusted using information about a previously-delivered neural modulation therapy. For example, an average neural modulation therapy dosage can be determined, such as over a preceding interval (e.g., an hour, a week, etc.). To maintain a neural modulation therapy dosage, one or more neural modulation therapy parameters can be adjusted at 985.

Figure 10:
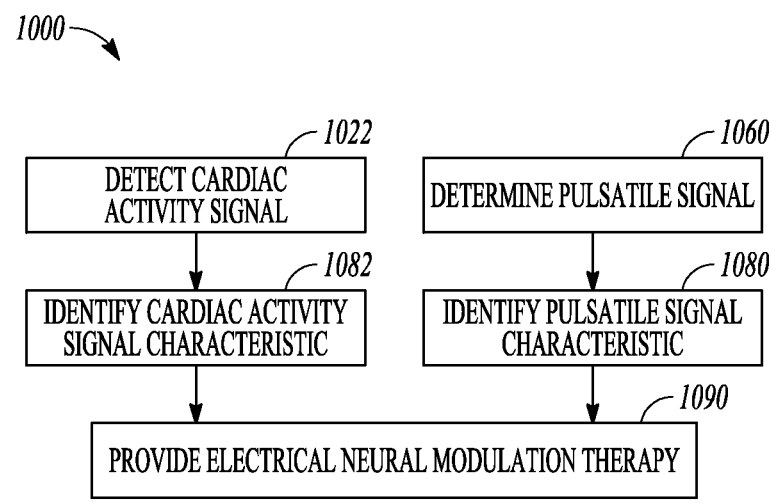
FIG. 10 illustrates generally an example that can include using information about cardiac activity and providing an electrical neural modulation therapy.

FIG. 10 illustrates generally an example that can include detecting cardiac activity. In an example, at 1060, a pulsatile signal can be determined, such as according to the discussion at 860. At 1080, a pulsatile signal feature can be identified, such as according to the discussion at 880.

At 1022, a cardiac activity signal can be detected. A cardiac activity signal can be determined in numerous ways, including using information about cardiac electrical activity, such as can be obtained using one or more electrodes coupled to the IMD 105, such as using the implantable lead system 108. A cardiac activity signal can be determined using other means, such as acoustically using heart sounds, mechanically using a pressure sensor, or as described above using cervical impedance. In an example, a cardiac activity signal can include an ECG signal, or other signal, such as a heart sound signal from which a cardiac activity signal can be inferred or determined.

At 1082, a cardiac activity signal characteristic can be identified. In an example, any signal characteristic can be used, such as including, among others, a timing, amplitude, frequency, shape, or integral of a portion of the cardiac activity signal. In an example, a sum, difference, linear combination, or product of identified cardiac activity signal characteristic can be used. In an example, at 1082, the processor circuit 110 can be used to identify at least one characteristic of the cardiac activity signal. Similarly, at 1080, the processor circuit 110 can optionally be used to identify at least one pulsatile signal characteristic. In response to the identified at least one characteristic, the processor circuit 110 can optionally adjust a neural modulation therapy parameter, or, at 1090, provide an electrical neural modulation therapy, such as using an adjusted neural modulation therapy parameter. In an example, information about cardiac activity can be used, such as together with a pulsatile signal characteristic, to time delivery of a neural modulation therapy.

In an example, a lower heart rate limit (LRL) can be used to modulate the electrical neural modulation therapy provided at 1090. In some examples, neural modulation therapy can reduce a patient heart rate. If a patient heart rate approaches or exceeds a LRL, a neural modulation therapy can be ceased or adjusted to avoid further reducing the heart rate. For example, if the detected cardiac activity at 1022 indicates that a patient heart rate has fallen below the LRL, a neural modulation therapy parameter can be adjusted, such as to terminate or adjust delivery of an electrical neural modulation therapy. Similarly, a maximum tracking rate (MTR) can be used to modulate the electrical neural modulation therapy provided at 1090. For example, if a patient heart rate approaches or exceeds the MTR, a neural modulation therapy can be terminated or adjusted. In an example, parameters associated with pacemaker therapy (e.g., LRL, MTR, etc.) can be received from an implanted pacemaker that can be separate from the IMD 105, or from a pacemaker therapy unit contained within the IMD 105.

Figure 11:
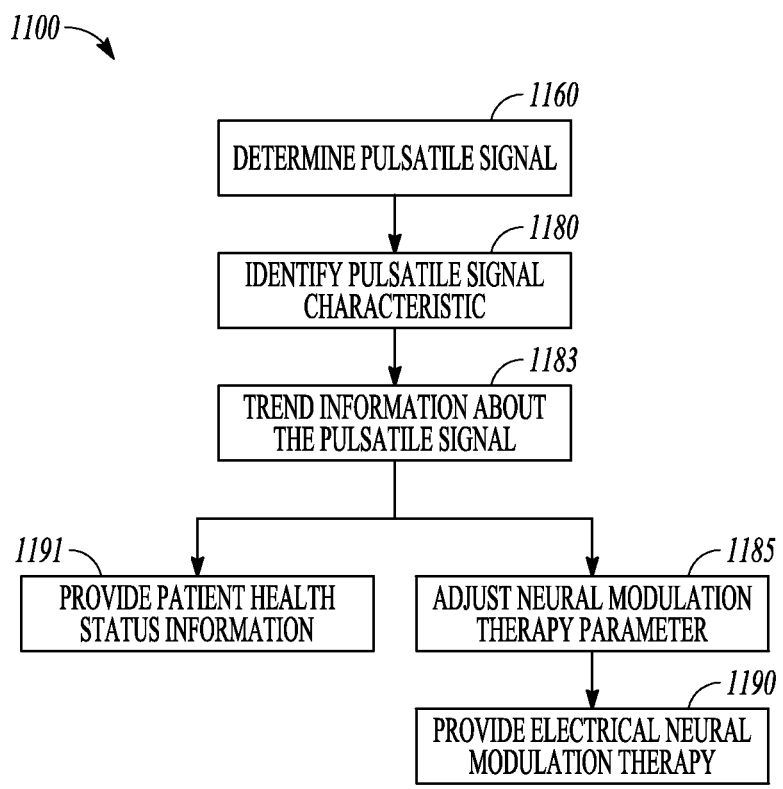
FIG. 11 illustrates generally an example that can include trending pulsatile information.

FIG. 11 illustrates generally an example that can include trending information about a pulsatile signal. At 1160, a pulsatile signal can be determined, such as according to the discussion at 860. At 1180, a pulsatile signal feature can be identified, such as according to the discussion at 880. At 1183, information about the pulsatile signal can be trended.

Figure 12:
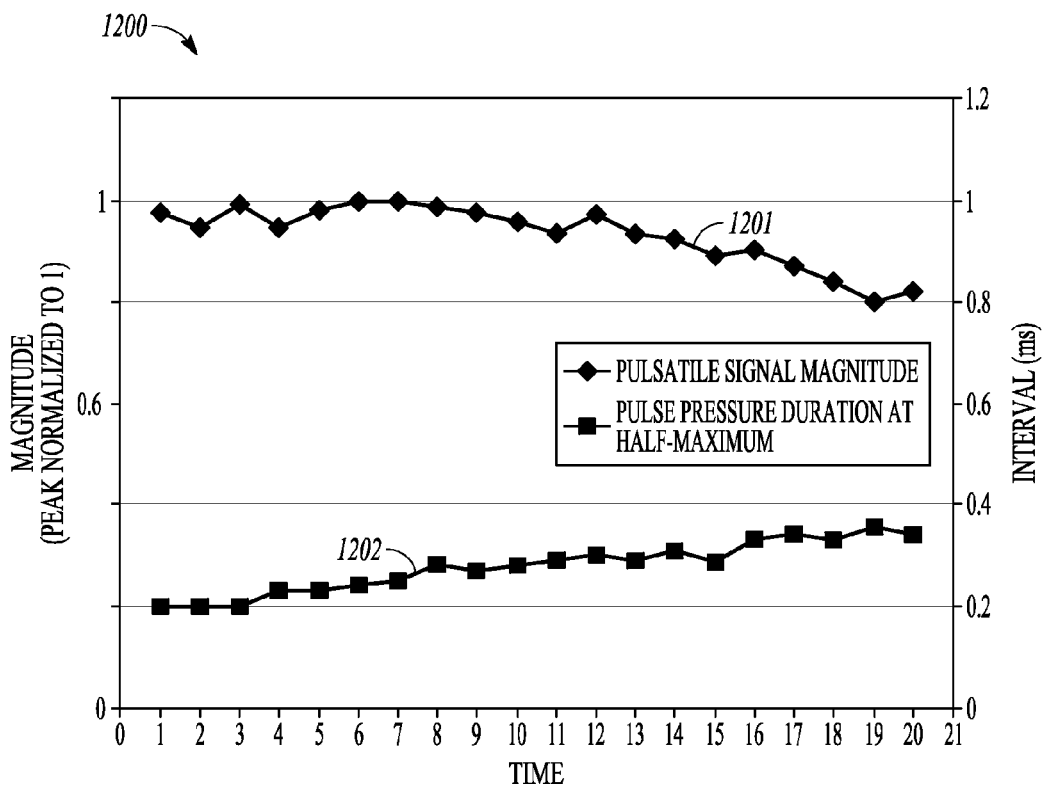
FIG. 12 illustrates generally an example that can include trending pulsatile information.
Figure 13:
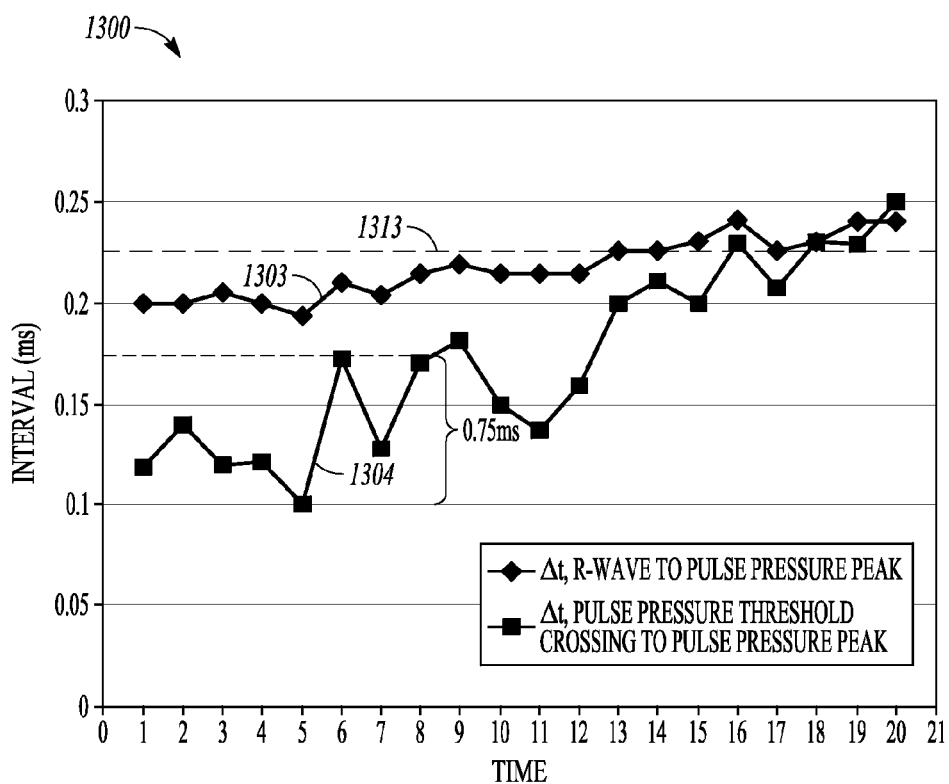
FIG. 13 illustrates generally an example that can include trending pulsatile information.

The information trended about the pulsatile signal at 1183 can include, for example, one or more pulsatile signal characteristics, or relationships between characteristics, such as between characteristics of a pulsatile signal and characteristics of another physiological signal. For example, a relationship between a pulsatile signal characteristic and a thoracic impedance signal characteristic can be trended. FIG. 13 illustrates several examples of information trended about a relationship between a pulsatile signal and an ECG signal. FIG. 12 illustrates several examples of information trended about characteristics of a pulsatile signal.

Returning to FIG. 11, at 1191, patient health status information can be provided, such as using the trended information about the pulsatile signal. In an example, the patient health status information can be provided to the patient, such as using various alerts emitted by the IMD 105, or using a device interface (e.g., using the external module 115). In an example, the patient health status information can be communicated to a caregiver, or the information can be stored, such as locally or externally, for later or concurrent processing, such as in a remote patient management system. In an example, the patient health status information provided at 1191 can include information about a change in the patient's pulsatile activity over time, such as to indicate an effectiveness of neural modulation therapy.

At 1185, a neural modulation therapy parameter can be adjusted, such as using the trended information about the pulsatile signal. For example, if the trended information indicates a patient status change by more than a threshold amount, a neural modulation therapy parameter can be adjusted, such as to increase an amplitude or a frequency of a neural modulation therapy signal. At 1190, an electrical neural modulation therapy can be provided to the patient, such as using the adjusted neural modulation therapy parameter.

FIG. 12 illustrates generally an example of trended information about a pulsatile signal. The example of FIG. 12 can include a chart 1200, such as including one or more pulsatile information trendlines. In an example, the chart 1200 can include a first pulsatile signal trendline 1201, such as can indicate a pulsatile signal magnitude trend. The pulsatile signal magnitude information can be normalized, such as shown in the example of FIG. 12. In an example, the x axis of the chart 1200 can represent discrete time intervals, such as corresponding to individual physiological cycles (e.g., a cardiac cycle), or other periods. For example, the first pulsatile signal trendline 1201 can represent pulsatile signal magnitude that has been recorded and trended, such as corresponding to a series of patient physiological cycles. In an example, the x axis can represent longer intervals. In an example, a central tendency of the pulsatile signal magnitude information can be recorded and trended, such as corresponding to hourly, daily, or weekly tendencies. In an example, an average of pulsatile signal magnitude information, such as over the course of an hour, can be recorded and trended, such as over the course of several hours.

In an example, the first pulsatile signal trendline 1201 can be used by the processor circuit 110 or a caregiver to recognize a change in a patient's health status, such as over a period of time. In the example of FIG. 12, a decreasing pulsatile signal magnitude can be observed.

In an example, the chart 1200 can include additional trendlines, such as a second pulsatile signal trendline 1202. In an example, the second pulsatile signal trendline 1202 can indicate a pulse pressure duration at half-maximum (e.g., the time interval $\Delta t_{(1/2)MAX}$ illustrated in the example of FIG. 4). In an example, the first and second pulsatile signal trendlines 1201 and 1202 can correspond to the same or different intervals, such as along the x axis of the chart 1200. In the example of FIG. 12, the pulse pressure duration at half-maximum increases over the trended period. In an example, information about one or more of the first and second trendlines 1201 and 1202 can be used to provide an indication of a patient health status (e.g., at 1191), or can be used to adjust a neural modulation therapy parameter (e.g., at 1185). In an example, the processor circuit 110 can be configured to interpret information about a pulsatile trend using additional information received from a physiological sensor, such as a patient heart rate sensor or posture sensor, such as to calibrate, adjust, or disregard a pulsatile signal trend. For example, during periods of transition between patient postures, pulsatile signal trend information can be disregarded.

FIG. 13 illustrates generally an example of trended information about a pulse pressure signal. In an example, a pulse pressure signal can be determined using a patient pulsatile signal. The example of FIG. 13 can include a chart 1300, such as including one or more pulse pressure trendlines. In an example, the chart can indicate a change in a pulse pressure characteristic interval, such as corresponding to a particular time interval along the x axis. In an example, the time interval can include a particular physiological cycle (e.g., a cardiac cycle), or some other time duration (e.g., a minute, a week, etc.). In an example where the time interval includes a particular or individual physiological cycle, the characteristic interval information can correspond to that physiological cycle. In an example where the time interval includes some other, longer duration, a central tendency or other indication of characteristic interval information over time can be used.

In an example, a third trendline 1303 can indicate a relationship over time of an interval between a detected R-wave peak and a corresponding pulse pressure peak (see, e.g., FIG. 3 at 311 and 331). That is, the third trendline 1303 can indicate a relationship or association between a cardiac electrical event and a pulse pressure, such as pulse pressure in a vessel distal to the heart. In an example, a neural modulation therapy parameter can be adjusted in response to a change in the third trendline 1303. For example, when the third trendline 1303 exceeds a threshold 1313 (e.g., in the example of FIG. 13, on or after time 13), a neural modulation therapy parameter can be adjusted, such as according to the discussion at 985 or 1185. In an example, information about a patient health status can be provided in response to changes in the third trendline 1303. For example, when the third trendline 1303 exceeds the threshold 1313, the information about the patient health status can be provided, such as according to the discussion at 1191.

The example of FIG. 13 can include a fourth trendline 1304, such as can indicate a relationship between relative characteristics of a pulse pressure signal. For example, the fourth trendline 1304 can include information about an interval between a pulse pressure threshold crossing and a pulse pressure peak, such as over a particular physiological cycle. As illustrated in FIG. 4, the interval can be between a pulsatile signal peak and a crossing of the pulsatile signal threshold 332 (e.g., the interval $\Delta t_4$ in FIG. 4).

In an example, a neural modulation therapy parameter can be adjusted in response to changes in the fourth trendline 1304. For example, when the fourth trendline 1304 indicates a change of more than threshold interval over a particular time window, a neural modulation therapy parameter can be adjusted, such as according to the discussion at 985 or 1185. For example, when the interval between the pulse pressure threshold crossing and the pulse pressure peak changes by more than about 0.75 ms, such as over fewer than five time intervals, a neural modulation therapy parameter can be adjusted or an electrical neural modulation therapy can be provided, or both. In an example, information about a patient health status can be provided in response to changes in the fourth trendline 1304. Additional information about a patient health status can be provided using other trends, such as comprising information about pulse pressure signal characteristics, pulsatile signal characteristics, or other physiological signal characteristics.

One of ordinary skill in the art will understand that software, hardware, firmware, or combinations thereof, can be used to implement the present subject matter. Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile, tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above detailed description is intended to be illustrative and not restrictive. Other embodiments will be apparent to those of skill in the art upon reading and understanding the above description. The scope of the invention should, therefore, be determined with reference to the appended claims, along with the full scope of equivalents to which such claims are entitled.

The claimed invention is:

1. An implantable apparatus comprising:
   an electrical test energy delivery circuit configured to provide an electrical test signal to a cervical location in a patient body;
   a detector circuit configured to use the electrical test signal to detect cervical impedance and generate a cervical impedance signal representing fluctuations in the detected cervical impedance over time;
   a therapy delivery circuit configured to provide electrical neural modulation therapy to the patient using a neural modulation timing parameter; and
   a processor circuit, coupled to the electrical test energy delivery circuit, the detector circuit, and the therapy delivery circuit, the processor circuit configured to:
   determine a pulsatile signal using the cervical impedance signal;
   identify at least one characteristic of the pulsatile signal; and
   control delivery of the neural modulation therapy using the neural modulation timing parameter and the at least one identified characteristic of the pulsatile signal.

2. The implantable apparatus of claim 1, wherein the processor circuit is configured to adjust a neural modulation therapy parameter in response to an identified characteristic of the pulsatile signal, and wherein the therapy delivery circuit is configured to provide the neural modulation therapy to the patient using the adjusted neural modulation therapy parameter.

3. The implantable apparatus of claim 2, wherein the processor circuit is configured to adjust the neural modulation therapy parameter using information about the patient's heart rate.

4. The implantable apparatus of claim 1, comprising a posture detection circuit configured to provide an indication of a patient posture, wherein the processor circuit is configured to adjust a neural modulation therapy parameter using the indication of the patient posture, and wherein the therapy delivery circuit is configured to provide the neural modulation therapy to the patient using the adjusted neural modulation therapy parameter.

5. The implantable apparatus of claim 1, wherein the processor circuit is configured to:
   identify a peak time of the pulsatile signal; and
   using an adjustable delay and the identified peak time, initiate or adjust delivery of the neural modulation therapy.

6. The implantable apparatus of claim 1, wherein the processor circuit is configured to initiate delivery of the neural modulation therapy in response to a first identified characteristic of the pulsatile signal, and to terminate delivery of the neural modulation therapy in response to a different second identified characteristic of the pulsatile signal.

7. The implantable apparatus of claim 1, wherein the detector circuit is configured to receive a signal representative of electrical activity of the patient's heart, and wherein the processor circuit is configured to:
   determine a cardiac activity indication using the received signal representative of electrical activity of the patient's heart; and
   control delivery of the neural modulation therapy using the neural modulation timing parameter, the determined cardiac activity indication, and the identified at least one characteristic of the pulsatile signal.

8. The implantable apparatus of claim 1, wherein the processor circuit is configured to trend information about the pulsatile signal over multiple cardiac cycles and to provide patient health status information using the trended information about the pulsatile signal.

9. The implantable apparatus of claim 8, wherein the processor circuit is configured to adjust a neural modulation therapy parameter in response to the information about the patient health status, and wherein the therapy delivery circuit is configured to provide the neural modulation therapy to the patient using the adjusted neural modulation therapy parameter.

10. The implantable apparatus of claim 1, wherein the therapy delivery circuit is configured to provide an autonomic neural modulation therapy to the patient in coordination with the patient's intrinsic neural activity.

11. The implantable apparatus of claim 1, wherein the therapy delivery circuit is configured to use the determined pulsatile signal to identify a cardiac refractory period and coordinate the neural modulation therapy with the cardiac refractory period.

12. The implantable apparatus of claim 1, wherein the electrical test energy delivery circuit is configured to provide the electrical test signal using an electrode disposed in a cervical region near enough to a carotid artery for the detector circuit to detect a dimensional change in the carotid artery.

13. The implantable apparatus of claim 1, wherein the processor circuit is configured to identify the at least one characteristic of the pulsatile signal, the at least one characteristic of the pulsatile signal including at least one of:
   a timing of a portion of the pulsatile signal;
   an amplitude of the pulsatile signal;
   a frequency determined using the pulsatile signal;
   a shape of the pulsatile signal;
   an integral of a portion of the pulsatile signal;
   a derivative of a portion of the pulsatile signal;
   a ratio of characteristics derived from the pulsatile signal; or
   a sum, difference, linear combination, or product of characteristics derived from the pulsatile signal.

14. The implantable apparatus of claim 1, further comprising an electrode configured to provide the electrical test signal to the cervical location;
   wherein the electrical test energy delivery circuit is configured to provide the electrical test signal using the electrode configured to provide the electrical test signal to the cervical location, and wherein the therapy delivery circuit is configured to provide the neural modulation therapy using the same electrode.

15. The implantable apparatus of claim 1, wherein the detector circuit is configured to receive a signal representative of a patient physical activity; and
   wherein the processor circuit is configured to:
      determine a patient physical activity status using the received signal representative of the patient physical activity; and
      control delivery of the neural modulation therapy using the neural modulation timing parameter, the determined patient physical activity status, and the identified at least one characteristic of the pulsatile signal.

16. The implantable apparatus of claim 1, wherein the processor circuit is configured to determine, as the pulsatile signal, a pulse pressure signal, using the cervical impedance signal.

17. A method comprising:
   delivering an electrical test signal to a cervical location within a patient body;
   using the electrical test signal to detect fluctuations in cervical impedance over time;
   determining a pulsatile signal using the detected fluctuations in cervical impedance;
   identifying at least one characteristic of the pulsatile signal; and
   providing an electrical neural modulation therapy using the at least one identified characteristic of the pulsatile signal.

18. The method of claim 17, comprising identifying a patient physiological cycle using the determined pulsatile signal, wherein the providing the electrical neural modulation therapy includes providing the electrical neural modulation therapy in coordination with the identified patient physiological cycle.

19. The method of claim 17, comprising:
   receiving a signal representative of electrical activity of the patient's heart; and
   determining a cardiac activity indication using the received signal representative of electrical activity of the patient's heart;
   wherein the providing the electrical neural modulation therapy includes using the determined cardiac activity indication.

20. An implantable apparatus comprising:
   a circuit configured to provide electrical signals including at least one electrical signal to a cervical location in a patient body, the circuit including a therapy delivery circuit configured to provide electrical neural modulation therapy to the patient using a neural modulation timing parameter;
   a detector circuit configured to use the at least one electrical signal provided to the cervical location to detect cervical impedance and generate a cervical impedance signal representing fluctuations in the detected cervical impedance over time; and
   a processor circuit, coupled to the electrical circuit and the detector circuit, the processor circuit configured to:
      determine a pulsatile signal using the cervical impedance signal;
      identify at least one characteristic of the pulsatile signal; and
      control delivery of the neural modulation therapy using the neural modulation timing parameter and the at least one identified characteristic of the pulsatile signal.

* * * * *